(12) United States Patent
Connolly et al.

(10) Patent No.: US 8,293,750 B2
(45) Date of Patent: Oct. 23, 2012

(54) PYRAZINES AS DELTA OPIOID RECEPTOR MODULATORS

(75) Inventors: Peter J. Connolly, New Providence, NJ (US); Shu-Chen Lin, Doylestown, PA (US); Mark J. Macielag, Branchburg, NJ (US); Yue-Mei Zhang, Belle Mead, NJ (US)

(73) Assignee: Janssen Pharmaceutica NV (BE)

( * ) Notice: Subject to any disclaimer, the term of this patent is extended or adjusted under 35 U.S.C. 154(b) by 0 days.

(21) Appl. No.: 13/451,652

(22) Filed: Apr. 20, 2012

(65) Prior Publication Data

US 2012/0202824 A1     Aug. 9, 2012

Related U.S. Application Data

(62) Division of application No. 12/913,917, filed on Oct. 28, 2010, now Pat. No. 8,183,371.

(60) Provisional application No. 61/256,392, filed on Oct. 30, 2009.

(51) Int. Cl.
*A61K 31/4965* (2006.01)

(52) U.S. Cl. .................. 514/255.05; 544/408; 544/405; 544/336; 514/252.1

(58) Field of Classification Search ............... 544/336, 544/498, 405; 514/248, 252.01
See application file for complete search history.

(56) References Cited

U.S. PATENT DOCUMENTS

| | | | |
|---|---|---|---|
| 6,465,467 | B1 | 10/2002 | Nilsson et al. |
| 7,015,227 | B2 | 3/2006 | Darrow et al. |
| 7,071,180 | B2 | 7/2006 | Nilsson et al. |
| 7,534,794 | B2 | 5/2009 | Nilsson et al. |
| 2003/0199511 | A1 | 10/2003 | Li et al. |
| 2006/0142307 | A1 | 6/2006 | Hellberg et al. |
| 2009/0239847 | A1* | 9/2009 | Bruce et al. ............... 514/218 |

FOREIGN PATENT DOCUMENTS

| | | |
|---|---|---|
| WO | WO 00/76984 A2 | 12/2000 |
| WO | WO 03/051366 A3 | 6/2003 |
| WO | WO 2004/000318 A2 | 12/2003 |
| WO | WO 2005/040151 A1 | 5/2005 |
| WO | WO 2008/046226 A1 | 4/2008 |

OTHER PUBLICATIONS

International Search Report dated Apr. 6, 2011 for corresponding Patent Application No. PCT/US2010/054469.
Evans, C.J.(1993), "Diversity Among the Opioid Receptors", in *Biological Basis of Substance Abuse*, eds. Koreman SG and Barchas J.D. (Oxford University Press, New York) pp. 31-48.
Gilbert, P. & Martin, W., "The Effects of Morphine- and Nalorphine-Like Drugs in the Nondependent, Morphine-Dependent and Cyclazocine-Dependent Chronic Spinal Dog", *J. Pharmacol Epx Ther.* 1976, vol. 198, pp. 66-82.
Gross, R., et al., "Dynorphin A and c-AMP-dependent Protein Kinase Independently Regulate Neuronal Calcium Currents", *Pro Natl Acad Sci USA*, 1990, vol. 87, pp. 7025-7029.
Lord, J., et al., "Endogenous Opioid Peptides; Multiple Agonists and Receptors", *Nature*, 1977, vol. 11, pp. 308-314.
Mansour, A., et al., "Anatomy of CNS Opioid Receptors", Trends in Neurosci, 1988, vol. 11, pp. 308-314.
Pert, C., et al., Opiate Receptor: Demonstration in Nervous Tissue, Science (1973)179:1011-1014.
Sharma, S., et al., "Dual Regulation of Adenylate Cyclase Accounts for Narcotic Dependence and Tolerance", *Proc Natl Acad Sci USA*, 1975, vol. 72, pp. 3092-3096.
Wollemann, M., "Recent Developments in th Research of Opioid Receptor Subtype Molecular Characterization", *J. Neurchem* 1990, vol. 54, pp. 1095-1101.

\* cited by examiner

*Primary Examiner* — James O Wilson
*Assistant Examiner* — Alexander R Pagano
(74) *Attorney, Agent, or Firm* — Joseph S. Kentoffio

(57) ABSTRACT

Disclosed are compounds, compositions and methods for treating various diseases, syndromes, conditions and disorders, including pain. Such compounds are represented by Formula I as follows:

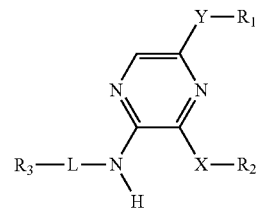

Formula I wherein $R_1$, $R_2$, $R_3$, L, X, and Y are defined herein.

3 Claims, No Drawings

PYRAZINES AS DELTA OPIOID RECEPTOR MODULATORS

CROSS REFERENCE TO RELATED APPLICATIONS

The present application is a divisional application of U.S. application Ser. No. 12/913,917 filed Oct. 28, 2010 now U.S. Pat. No. 8,183,371 which claims the benefit of U.S. Provisional Application No. 61/256,392, filed on Oct. 30, 2009. The complete disclosures of the aforementioned related patent applications are hereby incorporated herein by reference for all purposes.

FIELD OF THE INVENTION

The present invention is directed to novel opioid receptor modulators of Formula (I). The invention further relates to methods for preparing such compounds, pharmaceutical compositions containing them, and their use in the treatment of opioid modulated disorders.

BACKGROUND OF THE INVENTION

The term "opiate" has been used to designate pharmacologically active alkaloids derived from opium, e.g., morphine, codeine, and many semi-synthetic congeners of morphine. After the isolation of peptide compounds with morphine-like actions, the term opioid was introduced to refer generically to all drugs with morphine-like actions. Included among opioids are various peptides that exhibit morphine-like activity, such as endorphins, enkephalins and dynorphins. However, some sources use the term "opiate" in a generic sense, and in such contexts, opiate and opioid are interchangeable. Additionally, the term opioid has been used to refer to antagonists of morphine-like drugs as well as to characterize receptors or binding sites that combine with such agents.

Opioids are generally employed as analgesics, but they may have many other pharmacological effects as well. Morphine and related opioids produce certain of their major effects on the central nervous and digestive systems. The effects are diverse, including analgesia, drowsiness, mood changes, respiratory depression, dizziness, mental clouding, dysphoria, pruritus, increased pressure in the biliary tract, decreased gastrointestinal motility, nausea, vomiting, and alterations of the endocrine and autonomic nervous systems.

When therapeutic doses of morphine are given to patients with pain, they report that the pain is less intense, less discomforting, or entirely gone. In addition to experiencing relief of distress, some patients experience euphoria. However, when morphine in a selected pain-relieving dose is given to a pain-free individual, the experience is not always pleasant; nausea is common, and vomiting may also occur. Drowsiness, inability to concentrate, difficulty in mentation, apathy, lessened physical activity, reduced visual acuity, and lethargy may ensue.

Two distinct classes of opioid molecules can bind opioid receptors: the opioid peptides (e.g., the enkephalins, dynorphins, and endorphins) and the alkaloid opiates (e.g., morphine, etorphine, diprenorphine and naloxone). Subsequent to the initial demonstration of opiate binding sites (Pert, C. B. and Snyder, S. H., Science (1973) 179:1011-1014), the differential pharmacological and physiological effects of both opioid peptide analogues and alkaloid opiates served to delineate multiple opioid receptors. Accordingly, three molecularly and pharmacologically distinct opioid receptor types have been described: delta, kappa and mu. Furthermore, each type is believed to have sub-types (Wollemann, M., J Neurochem (1990) 54:1095-1101; Lord, J. A., et al., Nature (1977) 267:495-499).

All three of these opioid receptor types appear to share the same functional mechanisms at a cellular level. For example, the opioid receptors cause inhibition of adenylate cyclase, and inhibition of neurotransmitter release via both potassium channel activation and inhibition of $Ca^{2+}$ channels (Evans, C. J., In: Biological Basis of Substance Abuse, S. G. Korenman & J. D. Barchas, eds., Oxford University Press (in press); North, A. R., et al., Proc Natl Acad Sci USA (1990) 87:7025-29; Gross, R. A., et al., Proc Natl Acad Sci USA (1990) 87:7025-29; Sharma, S. K., et al., Proc Natl Acad Sci USA (1975) 72:3092-96). Although the functional mechanisms are the same, the behavioral manifestations of receptor-selective drugs differ greatly (Gilbert, P. E. & Martin, W. R., J Pharmacol Exp Ther (1976) 198:66-82). Such differences may be attributable in part to the anatomical location of the different receptors.

Delta receptors have a more discrete distribution within the mammalian CNS than either mu or kappa receptors, with high concentrations in the amygdaloid complex, striatum, substantia nigra, olfactory bulb, olfactory tubercles, hippocampal formation, and the cerebral cortex (Mansour, A., et al., Trends in Neurosci (1988) 11:308-14). The rat cerebellum is remarkably devoid of opioid receptors including delta opioid receptors.

There is a continuing need for new delta opioid receptor modulators as analgesics. There is a further need for delta opioid receptor selective agonists as analgesics having reduced side effects. There is also a need for delta opioid receptor antagonists as immunosuppressants, antiinflammatory agents, agents for the treatment of neurological and psychiatric conditions, agents for the treatment of urological and reproductive conditions, medicaments for drug and alcohol abuse, agents for treating gastritis and diarrhea, cardiovascular agents and agents for the treatment of respiratory diseases, having reduced side effects.

There is a continuing need for new opioid receptor modulators as analgesics. There is a further need for delta and mu opioid receptor agonists as analgesics having reduced side effects. There is a further need for mu opioid receptor agonists as analgesics having reduced side effects for the treatment of pain, immune function, esophageal reflux, and cough. There is also a need for delta opioid receptor agonists as analgesic agents, agents for the treatment of respiratory diseases, cardiovascular agents, agents for treating urological dysfunction, and agents for the treatment of neurological and psychiatric conditions. There is further need for dual delta opioid receptor/mu opioid receptor agonists.

SUMMARY OF THE INVENTION

The present invention is directed to a compound of Formula I

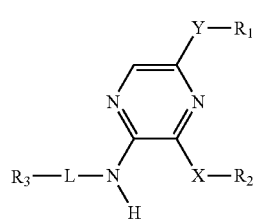

Formula I wherein
$R_1$ is selected from the group consisting of
i) phenyl optionally substituted with one to two substituents independently selected from the group consisting of $C_{1-4}$alkyl, $C_{1-4}$alkoxy, $C_{1-4}$alkylthio, hydroxy, chloro, and fluoro;

ii) pyridinyl optionally substituted with one substituent selected from the group consisting of $C_{1-4}$alkyl, $C_{1-4}$alkoxy, $C_{1-4}$alkylthio, hydroxy, fluoro, chloro, and cyano; and
iii) pyrimidin-5-yl;
or, $R_1$ is optionally methoxy-methyl when Y is ethynyl;
Y is ethynyl or a bond;
$R_2$ is phenyl, benzofuranyl, 2,3-dihydrobenzofuranyl, benzo[1,3]dioxol-5-yl, indolyl, or pyridinyl optionally substituted with methyl; wherein phenyl is optionally substituted with one to two substituents independently selected from the group consisting of $C_{1-4}$alkyl, $C_{1-4}$alkoxy, fluoro, chloro, cyano, cyanomethyl, difluoromethoxy, trifluoromethoxy, and hydroxy;
or $R_2$ is phenyl substituted with one $C_{1-4}$alkylcarbonylamino or 1H-imidazol-1-yl substituent;
X is O or $CH_2$;
L is absent and $R_3$ is 4-amino-cyclohexyl; or, L is methylene and $R_3$ is selected from the group consisting of
i) pyrrolidin-2-yl;
ii) 1-amino-eth-1-yl; and
iii) 1-amino-cyclopent-1-yl;
or, $R_3$ is cyclized with L and the nitrogen atom to which L is attached to form piperazinyl optionally substituted with 4-$C_{1-4}$alkyl;
and enantiomers, diastereomers, solvates, and pharmaceutically acceptable salts thereof.

The present invention is also directed to a pharmaceutical composition comprising a pharmaceutically acceptable carrier and a compound of Formula (I) or a pharmaceutically acceptable salt form thereof.

Also provided are processes for making a pharmaceutical composition comprising mixing a compound of Formula (I) and a pharmaceutically acceptable carrier.

The present invention is further directed to methods for treating or ameliorating an opioid receptor-modulated disorder. In particular, the methods of the present invention are directed to treating or ameliorating a opioid receptor-modulated disorder including, but not limited to, inflammatory pain, centrally mediated pain, peripherally mediated pain, visceral pain, structural related pain, cancer/pain, soft tissue injury related pain, progressive disease related pain, neuropathic pain and acute pain from acute injury, acute pain from trauma, acute pain from surgery, chronic pain from headache, chronic pain from neuropathic conditions, chronic pain from post-stroke conditions and chronic pain from migraine.

The present invention also provides methods for producing the instant compounds and pharmaceutical compositions and medicaments thereof.

As used herein, the following terms are intended to have the following meanings:

"$C_{a-b}$" (where a and b are integers) refers to a radical containing from a to b carbon atoms inclusive. For example, $C_{1-3}$ denotes a radical containing 1, 2 or 3 carbon atoms.

With reference to substituents, the term "independently" means that when more than one of such substituent is possible, such substituents may be the same or different from each other. Therefore, designated numbers of carbon atoms (e.g. $C_{1-8}$) shall refer independently to the number of carbon atoms in an alkyl or cycloalkyl moiety or to the alkyl portion of a larger substituent in which alkyl appears as its prefix root.

As used herein, unless otherwise noted, "alkyl" whether used alone or as part of a substituent group refers to straight and branched carbon chains having 1 to 8 carbon atoms or any number within this range. The term "alkoxy" refers to an —Oalkyl substituent group, wherein alkyl is as defined supra. Similarly, the terms "alkenyl" and "alkynyl" refer to straight and branched carbon chains having 2 to 8 carbon atoms or any number within this range, wherein an alkenyl chain has at least one double bond in the chain and an alkynyl chain has at least one triple bond in the chain. An alkyl and alkoxy chain may be substituted on a carbon atom. In substituent groups with multiple alkyl groups such as ($C_{1-6}$alkyl)$_2$amino- the $C_{1-6}$alkyl groups of the dialkylamino may be the same or different.

"Halogenated alkyl" refers to a saturated branched or straight chain alkyl radical derived by removal of 1 hydrogen atom from the parent alkane; the parent alkyl chain contains from 1 to 8 carbon atoms with 1 or more hydrogen atoms replaced with halogen atoms up to and including replacement of all hydrogen atoms with halogen. Preferred halogenated alkyl groups include trifluoromethyl substituted alkyls, difluoromethyl substituted alkyls, and perfluorinated alkyls; more preferred fluorinated alkyls include trifluoromethyl and difluoromethyl. "Halogenated alkoxy" refers to a radical derived from a halogenated alkyl, radical attached to an oxygen atom with the oxygen atom having one open valence for attachment to a parent structure.

The term "cycloalkyl" refers to saturated or partially unsaturated, moncyclic or polycyclic hydrocarbon of from 3 to 20 carbon atom members (preferably from 3 to 14 carbon atom members). Examples of such groups include, and are not limited to, cyclopropyl, cyclobutyl, cyclopentyl, cyclohexyl, cycloheptyl or adamantyl. The term cycloalkyl includes a cycloalkyl ring fused to a benzene ring (benzo fused cycloalkyl), or a 5 or 6 membered heteroaryl ring (containing one of O, S or N and, optionally, one additional nitrogen) to form a heteroaryl fused cycloalkyl.

The term "heterocyclyl" refers to a nonaromatic monocyclic ring of 5 to 10 members in which 1 to 4 members are nitrogen or a nonaromatic monocyclic ring of 5 to 10 members in which zero, one or two members are nitrogen and up to two members are oxygen or sulfur; wherein, optionally, the ring contains zero, one or two unsaturated bonds. The term heterocyclyl includes a heterocyclyl ring fused to a benzene ring (benzo fused heterocyclyl), a 5 or 6 membered heteroaryl ring (containing one of O, S or N and, optionally, one additional nitrogen), a 5 to 7 membered cycloalkyl or cycloalkenyl ring, a 5 to 7 membered heterocyclyl ring (of the same definition as above but absent the option of a further fused ring) or fused with the carbon of attachment of a cycloalkyl, cycloalkenyl or heterocyclyl ring to form a spiro moiety. For instant compounds of the invention, the carbon atom ring members that form the heterocyclyl ring are fully saturated. Other compounds of the invention may have a partially saturated heterocyclyl ring. Additionally, heterocyclyl includes a heterocyclic ring bridged to form bicyclic rings. Preferred partially saturated heterocyclyl rings may have from one to two double bonds. Such compounds are not considered to be fully aromatic and are not referred to as heteroaryl compounds. Examples of heterocyclyl groups include, and are not limited to, pyrrolinyl (including 2H-pyrrole, 2-pyrrolinyl or 3-pyrrolinyl), pyrrolidinyl, 2-imidazolinyl, imidazolidinyl, 2-pyrazolinyl, pyrazolidinyl, piperidinyl, morpholinyl, thiomorpholinyl and piperazinyl.

The term "aryl" refers to an unsaturated, aromatic monocyclic ring of 6 carbon members or to an unsaturated, aromatic polycyclic ring of from 10 to 14 carbon members. Examples of such aryl rings include, and are not limited to, phenyl, naphthalenyl or anthracenyl. Preferred aryl groups for the practice of this invention are phenyl and naphthalenyl.

The term "heteroaryl" refers to an aromatic ring of 5 or 6 members wherein the ring consists of carbon atoms and has at least one heteroatom member. Suitable heteroatoms include nitrogen, oxygen or sulfur. In the case of 5 membered rings, the heteroaryl ring contains one member of nitrogen, oxygen or sulfur and, in addition, may contain up to three additional nitrogens. In the case of 6 membered rings, the heteroaryl ring may contain from one to three nitrogen atoms. For the case wherein the 6 membered ring has three nitrogens, at most two nitrogen atoms are adjacent. The term heteroaryl includes a heteroaryl ring fused to a benzene ring (benzofused heteroaryl), a 5 or 6 membered heteroaryl ring (containing one of O, S or N and, optionally, one additional nitrogen), a 5 to 7 membered cycloalkyl ring or a 5 to 7 membered heterocyclic ring (as defined supra but absent the option of a further fused ring). Examples of heteroaryl groups include, and are not limited to, furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl or pyrazinyl; fused heteroaryl groups include indolyl, isoindolyl, benzofuryl, benzothienyl, indazolyl, benzimidazolyl, benzothiazolyl, benzoxazolyl, benzisoxazolyl, benzothiadiazolyl, benzotriazolyl, quinoxalinyl, quinolinyl, isoquinolinyl or quinazolinyl.

The term "arylalkyl" means an alkyl group substituted with an aryl group (e.g., benzyl, phenethyl). Similarly, the term "arylalkoxy" indicates an alkoxy group substituted with an aryl group (e.g., benzyloxy).

The term "halogen" refers to fluorine, chlorine, bromine and iodine. Substituents that are substituted with multiple halogens are substituted in a manner that provides compounds, that are stable.

The term "oxo" whether used alone or as part of a substituent group refers to an O═ to either a carbon or a sulfur atom. For example, phthalimide and saccharin are examples of compounds with oxo substituents.

Whenever the term "alkyl" or "aryl" or either of their prefix roots appear in a name of a substituent (e.g., arylalkyl, alkylamino) it shall be interpreted as including those limitations given above for "alkyl" and "aryl." Designated numbers of carbon atoms (e.g., $C_1$-$C_6$) shall refer independently to the number of carbon atoms in an alkyl moiety or to the alkyl portion of a larger substituent in which alkyl appears as its prefix root. For alkyl and alkoxy substituents the designated number of carbon atoms includes all of the independent members included in the range specified individually and all the combination of ranges within the range specified. For example $C_{1-6}$ alkyl would include methyl, ethyl, propyl, butyl, pentyl and hexyl individually as well as sub-combinations thereof (e.g. $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

As used herein, the term "acyl" refers to alkylcarbonyl substituents.

Throughout this disclosure, the terminal portion of the designated side chain is described first, followed by the adjacent functionality toward the point of attachment. Thus, for example, a "phenyl($C_{1-6}$)alkylaminocarbonyl($C_{1-6}$)alkyl" substituent refers to a group of the formula

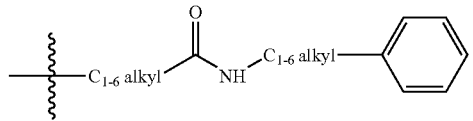

Unless otherwise noted, it is intended that the definition of any substituent or variable at a particular location in a molecule be independent of its definitions elsewhere in that molecule. It is understood that substituents and substitution patterns on the compounds of formula (I) can be selected by one of ordinary skill in the art to provide compounds that are chemically stable and that can be readily synthesized by techniques known in the art as well as those methods set forth herein.

For purposes of the present invention, the term "opioid receptor-modulated" is used to refer to the condition of being affected by the modulation of an opioid receptor, including but not limited to, the state of being mediated by the opioid receptor.

DETAILED DESCRIPTION OF THE INVENTION

Embodiments of the present invention include those compounds of Formula (I)

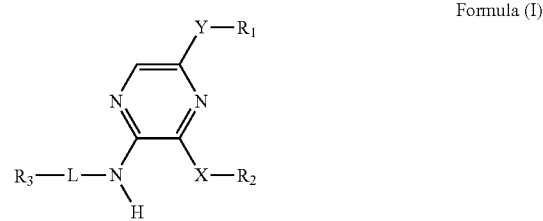

Formula (I)

wherein
a) $R_1$ is selected from the group consisting of
   i) phenyl;
   ii) pyridinyl optionally substituted with one substituent selected from the group consisting of $C_{1-4}$alkoxy, fluoro, chloro, and cyano; and
   iii) pyrimidin-5-yl;
   or, $R_1$ is optionally methoxy-methyl when Y is ethynyl;
b) $R_1$ is selected from the group consisting of
   i) phenyl;
   ii) pyridinyl optionally substituted with one substituent selected from the group consisting of $C_{1-4}$alkoxy and cyano; and
   iii) pyrimidin-5-yl;
c) $R_1$ is selected from the group consisting of
   i) phenyl;
   ii) pyridinyl optionally substituted with one substituent selected from the group consisting of methoxy and cyano; and
   iii) pyrimidin-5-yl;
d) Y is a bond;
e) $R_2$ is phenyl, benzofuranyl, 2,3-dihydrobenzofuranyl, benzo[1,3]dioxol-5-yl, indolyl, or pyridinyl optionally substituted with methyl; wherein phenyl is optionally substituted with one to two substituents independently selected from the group consisting of $C_{1-4}$alkyl, $C_{1-4}$alkoxy, fluoro, chloro, cyano, cyanomethyl, difluoromethoxy, trifluoromethoxy, and hydroxy;
   or, $R_2$ is phenyl substituted with one $C_{1-4}$alkylcarbonylamino substituent;
f) $R_2$ is phenyl optionally substituted with one to two substituents independently selected from the group consisting of $C_{1-4}$alkyl, $C_{1-4}$alkoxy, fluoro, chloro, cyano, cyanomethyl, difluoromethoxy, trifluoromethoxy, and hydroxy;
   or, $R_2$ is phenyl substituted with one $C_{1-4}$alkylcarbonylamino substituent;
g) $R_2$ is phenyl optionally substituted with one substituent selected from the group consisting of $C_{1-4}$alkyl, $C_{1-4}$alkoxy, fluoro, chloro, cyano, cyanomethyl, difluoromethoxy, trifluoromethoxy, and hydroxy;
h) X is O;
i) L is methylene and $R_3$ is selected from the group consisting of
   i) pyrrolidin-2-yl;
   ii) 1-amino-eth-1-yl; and
   iii) 1-amino-cyclopent-1-yl;
   or, $R_3$ is cyclized with L and the nitrogen atom to which L is attached to form piperazinyl;
   and any combination of embodiments a) through i) above, provided that it is understood that combinations in which different embodiments of the same substituent would be combined are excluded; and enantiomers, diastereomers, solvates, and pharmaceutically acceptable salts thereof.

A further embodiment of the present invention includes compounds of Formula (I)

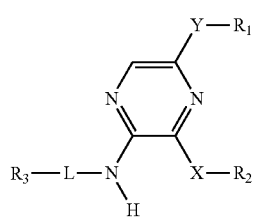

Formula (I)

wherein
$R_1$ is selected from the group consisting of
i) phenyl;
ii) pyridinyl optionally substituted with one substituent selected from the group consisting of $C_{1-4}$alkoxy, fluoro, chloro, and cyano; and
iii) pyrimidin-5-yl;
or, $R_1$ is optionally methoxy-methyl when Y is ethynyl;
Y is a bond or ethynyl;
$R_2$ is phenyl, benzofuranyl, 2,3-dihydrobenzofuranyl, benzo[1,3]dioxol-5-yl, indolyl, or pyridinyl optionally substituted with methyl; wherein phenyl is optionally substituted with one to two substituents independently selected from the group consisting of $C_{1-4}$alkyl, $C_{1-4}$alkoxy, fluoro, chloro, cyano, cyanomethyl, difluoromethoxy, trifluoromethoxy, and hydroxy;
or, $R_2$ is phenyl substituted with one $C_{1-4}$alkylcarbonylamino substituent;
X is O or $CH_2$;
L is absent and $R_3$ is 4-amino-cyclohexyl; or L is methylene and $R_3$ is selected from the group consisting of
   i) pyrrolidin-2-yl;
   ii) 1-amino-eth-1-yl; and
   iii) 1-amino-cyclopent-1-yl;

or, $R_3$ is cyclized with L and the nitrogen atom to which L is attached to form piperazinyl; and enantiomers, diastereomers, solvates, and pharmaceutically acceptable salts thereof.

A further embodiment of the present invention includes compounds of Formula (I)

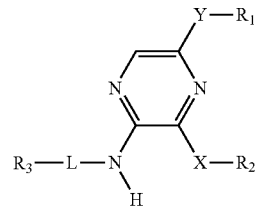

Formula (I)

wherein
$R_1$ is selected from the group consisting of
i) phenyl;
ii) pyridinyl optionally substituted with one substituent selected from the group consisting of $C_{1-4}$alkoxy and cyano; and
iii) pyrimidin-5-yl;
Y is a bond;
$R_2$ is phenyl optionally substituted with one to two substituents independently selected from the group consisting of $C_{1-4}$alkyl, $C_{1-4}$alkoxy, fluoro, chloro, cyano, cyanomethyl, difluoromethoxy, trifluoromethoxy, and hydroxy;
or, $R_2$ is phenyl substituted with one $C_{1-4}$alkylcarbonylamino substituent;
X is O;
L is methylene and $R_3$ is selected from the group consisting of
i) pyrrolidin-2-yl;
ii) 1-amino-eth-1-yl; and
iii) 1-amino-cyclopent-1-yl;
or, $R_3$ is cyclized with L and the nitrogen atom to which L is attached to form piperazinyl; and enantiomers, diastereomers, solvates, and pharmaceutically acceptable salts thereof.

A further embodiment of the present invention includes compounds of Formula (I)

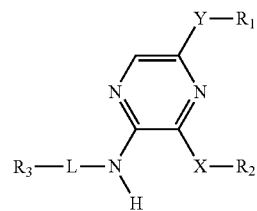

Formula (I)

wherein
$R_1$ is selected from the group consisting of
i) phenyl;
ii) pyridinyl optionally substituted with one substituent selected from the group consisting of methoxy and cyano; and
iii) pyrimidin-5-yl;
Y is a bond;
$R_2$ is phenyl optionally substituted with one substituent selected from the group consisting of $C_{1-4}$alkyl, $C_{1-4}$alkoxy, fluoro, chloro, cyano, cyanomethyl, difluoromethoxy, trifluoromethoxy, and hydroxy;

X is O;
L is methylene and R₃ is selected from the group consisting of
i) pyrrolidin-2-yl;
ii) 1-amino-eth-1-yl; and
iii) 1-amino-cyclopent-1-yl;
or, R₃ is cyclized with L and the nitrogen atom to which L is attached to form piperazinyl; and enantiomers, diastereomers, solvates, and pharmaceutically acceptable salts thereof.

A further embodiment of the present invention includes compounds of Formula (I)

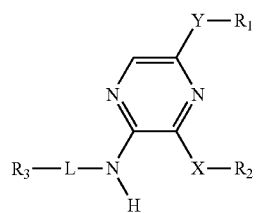

Formula (I)

selected from the group consisting of
a compound wherein R₁ is 6-methoxy-pyridin-3-yl, Y is a bond, R₂ is 4-methoxyphenyl, X is O, L is methylene, and R₃ is pyrrolidin-2-yl; (2S)
a compound wherein R₁ is pyridin-3-yl, Y is a bond, R₂ is 4-methoxyphenyl, X is O, L is methylene, and R₃ is pyrrolidin-2-yl; (2S)
a compound wherein R₁ is pyridin-3-yl, Y is ethynyl, R₂ is 4-methoxyphenyl, X is O, L is methylene, and R₃ is pyrrolidin-2-yl; (2S)
a compound wherein R₁ is methoxy-methyl, Y is ethynyl, R₂ is 4-methoxyphenyl, X is O, L is methylene, and R₃ is pyrrolidin-2-yl; (2S)
a compound wherein R₁ is pyrimidin-5-yl, Y is a bond, R₂ is 4-methoxyphenyl, X is O, L is methylene, and R₃ is pyrrolidin-2-yl; (2S)
a compound wherein R₁ is pyrimidin-5-yl, Y is a bond, R₂ is 4-ethylphenyl, X is O, L is methylene, and R₃ is pyrrolidin-2-yl; (2S)
a compound wherein R₁ is pyrimidin-5-yl, Y is a bond, R₂ is benzo[1,3]dioxol-5-yl, X is O, L is methylene, and R₃ is pyrrolidin-2-yl; (2S)
a compound wherein R₁ is pyrimidin-5-yl, Y is a bond, R₂ is 3-fluoro-4-methoxyphenyl, X is O, L is methylene, and R₃ is pyrrolidin-2-yl; (2S)
a compound wherein R₁ is pyrimidin-5-yl, Y is a bond, R₂ is 2-fluoro-4-methoxyphenyl, X is O, L is methylene, and R₃ is pyrrolidin-2-yl; (2S)
a compound wherein R₁ is pyrimidin-5-yl, Y is a bond, R₂ is 4-chlorophenyl, X is O, L is methylene, and R₃ is pyrrolidin-2-yl; (2S)
a compound wherein R₁ is pyrimidin-5-yl, Y is a bond, R₂ is 3-chlorophenyl, X is O, L is methylene, and R₃ is pyrrolidin-2-yl; (2S)
a compound wherein R₁ is pyrimidin-5-yl, Y is a bond, R₂ is 2-chlorophenyl, X is O, L is methylene, and R₃ is pyrrolidin-2-yl; (2S)
a compound wherein R₁ is pyrimidin-5-yl, Y is a bond, R₂ is 3-methylcarbonylamino-phenyl, X is O, L is methylene, and R₃ is pyrrolidin-2-yl; (2S)
a compound wherein R₁ is pyrimidin-5-yl, Y is a bond, R₂ is 4-(1H-imidazol-1-yl)phenyl, X is O, L is methylene, and R₃ is pyrrolidin-2-yl; (2S)
a compound wherein R₁ is pyrimidin-5-yl, Y is a bond, R₂ is 3-hydroxyphenyl, X is O, L is methylene, and R₃ is pyrrolidin-2-yl; (2S)
a compound wherein R₁ is pyridin-3-yl, Y is a bond, R₂ is 4-methoxyphenyl, X is CH₂, L is methylene, and R₃ is pyrrolidin-2-yl; (2S)
a compound wherein R₁ is pyrimidin-5-yl, Y is a bond, R₂ is 4-methoxyphenyl, X is CH₂, L is methylene, and R₃ is pyrrolidin-2-yl; (2S)
a compound wherein R₁ is pyrimidin-5-yl, Y is a bond, R₂ is 4-cyanophenyl, X is O, L is methylene, and R₃ is pyrrolidin-2-yl; (2S)
a compound wherein R₁ is 5-cyano-pyridin-3-yl, Y is a bond, R₂ is 4-methoxyphenyl, X is O, L is methylene, and R₃ is 1-amino-eth-1-yl; (1S)
a compound wherein R₁ is pyrimidin-5-yl, Y is a bond, R₂ is 4-methoxyphenyl, X is O, L is methylene, and R₃ is 1-amino-eth-1-yl; (1S)
a compound wherein R₁ is 5-cyano-pyridin-3-yl, Y is a bond, R₂ is 4-methoxyphenyl, X is O, L is methylene, and R₃ is 1-amino-cyclopent-1-yl;
a compound wherein R₁ is pyrimidin-5-yl, Y is a bond, R₂ is 4-methoxyphenyl, X is O, L is methylene, and R₃ is 1-amino-cyclopent-1-yl;
a compound wherein R₁ is 5-cyano-pyridin-3-yl, Y is a bond, R₂ is 4-methoxyphenyl, X is CH₂, L is methylene, and R₃ is pyrrolidin-2-yl; (2S)
a compound wherein R₁ is 5-cyano-pyridin-3-yl, Y is a bond, R₂ is 4-methoxyphenyl, X is O, L is methylene, and R₃ is pyrrolidin-2-yl; (2S)
a compound wherein R₁ is 5-cyano-pyridin-3-yl, Y is a bond, R₂ is 3-fluoro-4-methoxyphenyl, X is O, L is methylene, and R₃ is pyrrolidin-2-yl; (2S)
a compound wherein R₁ is 5-cyano-pyridin-3-yl, Y is a bond, R₂ is 2-fluoro-4-methoxyphenyl, X is O, L is methylene, and R₃ is pyrrolidin-2-yl; (2S)
a compound wherein R₁ is 5-cyano-pyridin-3-yl, Y is a bond, R₂ is 4-cyanomethyl-phenyl, X is O, L is methylene, and R₃ is pyrrolidin-2-yl; (2S)
a compound wherein R₁ is 5-cyano-pyridin-3-yl, Y is a bond, R₂ is 6-methyl-pyridin-3-yl, X is O, L is methylene, and R₃ is pyrrolidin-2-yl; (2S)
a compound wherein R₁ is 5-cyano-pyridin-3-yl, Y is a bond, R₂ is 4-difluoromethoxy-phenyl, X is O, L is methylene, and R₃ is pyrrolidin-2-yl; (2S)
a compound wherein R₁ is 5-cyano-pyridin-3-yl, Y is a bond, R₂ is 4-methoxyphenyl, X is O, and R₃ is cyclized with L and the nitrogen atom to which L is attached to form piperazin-1-yl;
a compound wherein R₁ is pyridin-3-yl, Y is a bond, R₂ is 4-methoxyphenyl, X is O, and R₃ is cyclized with L and the nitrogen atom to which L is attached to form piperazin-1-yl;
a compound wherein R₁ is pyrimidin-5-yl, Y is a bond, R₂ is benzofuran-5-yl, X is O, L is methylene, and R₃ is pyrrolidin-2-yl; (2S)
a compound wherein R₁ is pyrimidin-5-yl, Y is a bond, R₂ is 2,3-dihydro-benzofuran-5-yl, X is O, L is methylene, and R₃ is pyrrolidin-2-yl; (2S)
a compound wherein R₁ is 5-cyano-pyridin-3-yl, Y is a bond, R₂ is 4-methoxyphenyl, X is O, L is absent, and R₃ is trans-4-amino-cyclohexyl;
a compound wherein R₁ is 5-cyano-pyridin-3-yl, Y is a bond, R₂ is 4-methoxyphenyl, X is O, L is absent, and R₃ is cis-4-amino-cyclohexyl;

a compound wherein $R_1$ is 5-cyano-pyridin-3-yl, Y is a bond, $R_2$ is 4-trifluoromethoxy-phenyl, X is O, L is methylene, and $R_3$ is pyrrolidin-2-yl; (2S)

a compound wherein $R_1$ is 5-cyano-pyridin-3-yl, Y is a bond, $R_2$ is 4-ethylphenyl, X is O, L is methylene, and $R_3$ is pyrrolidin-2-yl; (2S)

a compound wherein $R_1$ is 5-cyano-pyridin-3-yl, Y is a bond, $R_2$ is 3-hydroxyphenyl, X is O, L is methylene, and $R_3$ is pyrrolidin-2-yl; (2S)

a compound wherein $R_1$ is 5-cyano-pyridin-3-yl, Y is a bond, $R_2$ is benzofuran-5-yl, X is O, L is methylene, and $R_3$ is pyrrolidin-2-yl; (2S)

a compound wherein $R_1$ is 5-cyano-pyridin-3-yl, Y is a bond, $R_2$ is indol-5-yl, X is O, L is methylene, and $R_3$ is pyrrolidin-2-yl; (2S)

a compound wherein $R_1$ is 5-cyano-pyridin-3-yl, Y is a bond, $R_2$ is 2-chlorophenyl, X is O, L is methylene, and $R_3$ is pyrrolidin-2-yl; (2S) and a compound wherein $R_1$ is 5-cyano-pyridin-3-yl, Y is a bond, $R_2$ is 3-chlorophenyl, X is O, L is methylene, and $R_3$ is pyrrolidin-2-yl; (2S)

and pharmaceutically acceptable salts thereof.

For use in medicine, salts of compounds of formula (I) refer to non-toxic "pharmaceutically acceptable salts." Other salts may, however, be useful in the preparation of compounds of formula (I) or of their pharmaceutically acceptable salts thereof. Suitable pharmaceutically acceptable salts of compounds of formula (I) include acid addition salts which can, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid.

Furthermore, where the compounds of formula (I) carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases which may be used in the preparation of pharmaceutically acceptable salts include the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid;

and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, sodium hydroxide, triethanolamine, tromethamine and zinc hydroxide.

Embodiments of the present invention include prodrugs of compounds of formula (I). In general, such prodrugs will be functional derivatives of the compounds that are readily convertible in vivo into the required compound. Thus, in the methods of treatment of embodiments of the present invention, the term "administering" encompasses the treatment of the various disorders described with the compound specifically disclosed or with a compound which may not be specifically disclosed, but which converts to the specified compound in vivo after administration to a patient. Conventional procedures for the selection and preparation of suitable prodrug derivatives are described, for example, in "Design of Prodrugs", ed. H. Bundgaard, Elsevier, 1985.

Where the compounds according to embodiments of this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention. The skilled artisan will understand that the term compound as used herein, is meant to include solvated compounds of Formula I.

Where the processes for the preparation of the compounds according to certain embodiments of the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

One embodiment of the present invention is directed to a composition comprising the (+)-enantiomer of a compound of formula (I) wherein said composition is substantially free from the (−)-isomer of said compound. In the present context, substantially free means less than 25%, preferably less than 10%, more preferably less than 5%, even more preferably less than 2% and even more preferably less than 1% of the (−)-isomer calculated as.

$$\% \ (+) - \text{enantiomer} = \frac{(\text{mass}(+) - \text{enantiomer})}{(\text{mass}(+) - \text{enantiomer}) + (\text{mass}(-) - \text{enantiomer})} \times 100$$

Another embodiment of the present invention is a composition comprising the (−)-enantiomer of a compound of formula (I) wherein said composition is substantially free from the (+)-isomer of said compound. In the present context, substantially free from means less than 25%, preferably less than 10%, more preferably less than 5%, even more preferably less than 2% and even more preferably less than 1% of the (+)-isomer calculated as $$\% \ (-) - \text{enantiomer} = \frac{(\text{mass}(-) - \text{enantiomer})}{(\text{mass}(+) - \text{enantiomer}) + (\text{mass}(-) - \text{enantiomer})} \times 100.$$

During any of the processes for preparation of the compounds of embodiments of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Even though the compounds of embodiments of the present invention (including their pharmaceutically acceptable salts and pharmaceutically acceptable solvates) can be administered alone, they will generally be administered in admixture with a pharmaceutical carrier, excipient or diluent selected with regard to the intended route of administration and standard pharmaceutical practice. Thus, particular embodiments of the present invention are directed to pharmaceutical compositions comprising compounds of formula (I) and one or more than one pharmaceutically acceptable carrier, excipient or diluent.

By way of example, in the pharmaceutical and veterinary compositions of embodiments of the present invention, the compounds of formula (I) may be admixed with any suitable binder(s), lubricant(s), suspending agent(s), coating agent(s), and/or solubilizing agent(s).

Tablets or capsules of the compounds may be administered one or two or more at a time, as appropriate. It is also possible to administer the compounds in sustained release formulations.

Alternatively, compounds of formula (I) can be administered by inhalation (intratracheal or intranasal) or in the form of a suppository or pessary, or they may be applied topically in the form of a lotion, solution, cream, ointment or dusting powder. For example, they can be incorporated into a cream consisting of an aqueous emulsion of polyethylene glycols or liquid paraffin. They can also be incorporated, at a concentration of between 1% and 10% by weight, into an ointment consisting of a white wax or white soft paraffin base together with such stabilizers and preservatives as may be required. An alternative means of transdermal administration is by use of a skin patch.

For some applications, preferably the compositions are administered orally in the form of tablets containing excipients such as starch or lactose, or in capsules or ovules either alone or in admixture with excipients, or in the form of elixirs, solutions or suspensions containing flavoring or coloring agents.

The compositions (as well as the compounds alone) can also be injected parenterally, for example intracavernosally, intravenously, intramuscularly, subcutaneously, intradermally or intrathecally. In this case, the compositions will comprise a suitable carrier or diluent.

For parenteral administration, the compositions are best used in the form of a sterile aqueous solution which may contain other substances, for example, enough salts or monosaccharides to make the solution isotonic with blood.

For buccal or sublingual administration, the compositions may be administered in the form of tablets or lozenges, which can be formulated in a conventional manner.

By way of further example, pharmaceutical and veterinary compositions containing one or more of the compounds of formula (I) as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral, etc.). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations also may be coated with substances such as sugars or be enterically-coated so as to modulate the major site of absorption. For parenteral administration, the carrier will usually consist of sterile water, and other ingredients may be added to increase solubility or preservation. Injectable suspensions or solutions may also be prepared utilizing aqueous carriers along with appropriate additives.

A therapeutically effective amount of compounds of formula (I) or a pharmaceutical composition thereof comprises a dose range from about 0.1 mg to about 3000 mg, in particular from about 1 mg to about 1000 mg or, more particularly, from about 10 mg to about 500 mg of active ingredient in a regimen of about 1 to 4 times per day for an average (70 kg) human; although, it is apparent to one skilled in the art that the therapeutically effective amount for active compounds of the invention will vary as will the conditions being treated.

For oral administration, a pharmaceutical composition is preferably provided in the form of tablets containing 0.01, 10.0, 50.0, 100, 150, 200, 250, and 500 milligrams of the active ingredient for the symptomatic adjustment of the dosage to the subject to be treated.

Advantageously, compounds of formula (I) may be administered in a single daily dose, or the total daily dosage may be administered in divided doses of two, three or four times daily. Furthermore, compounds of formula (I) can be administered in intranasal form via topical use of suitable intranasal vehicles, or via transdermal skin patches well known to those skilled in that art.

It is also apparent to one skilled in the art that the therapeutically effective dose for active compounds of formula (I) or a pharmaceutical composition thereof will vary according to the desired effect. Therefore, optimal dosages to be administered may be readily determined and will vary with the particular compound used, the mode of administration, the strength of the preparation, and the advancement of the disease condition. In addition, factors associated with the particular subject being treated, including subject age, weight, diet and time of administration, will result in the need to adjust the dose to achieve an appropriate therapeutic level. The above dosages are thus exemplary of the average case. There can be, of course, individual instances wherein higher or lower dosage ranges are merited, and such are within the scope of this invention.

Compounds of formula (I) may be administered in any of the foregoing compositions and dosage regimens or by means of those compositions and dosage regimens established in the art whenever use of the compounds of formula (I) as analgesics is required for a subject in need thereof.

Examples of pain intended to be within the scope of the present invention include, but are not limited to, inflammatory pain, centrally mediated pain, peripherally mediated pain, visceral pain, structural or soft tissue injury related pain, progressive disease related pain, neuropathic pain and acute pain such as caused by acute injury, trauma or surgery and chronic pain such as headache and that caused by neuropathic conditions, post-stroke conditions, cancer, and migraine.

Compounds of the present invention are also useful as immunosuppressants, antiinflammatory agents, agents for the treatment and prevention of neurological and psychiatric conditions, for instance, depression and Parkinson's disease, agents for the treatment of urological and reproductive conditions, for instance, urinary incontinence and premature ejaculation, medicaments for drug and alcohol abuse, agents for treating gastritis and diarrhea, cardiovascular agents and cardioprotective agents and agents for the treatment of respiratory diseases.

The compounds of the present invention are also useful in treating pain caused by osteoarthritis, rheumatoid arthritis, fibromyalgia, migraine, headache, toothache, burn, sunburn, snake bite (in particular, venomous snake bite), spider bite, insect sting, neurogenic bladder, benign prostatic hypertrophy, interstitial cystitis, rhinitis, contact dermatitis/hypersensitivity, itch, eczema, pharyngitis, mucositis, enteritis, cellulitis, causalgia, sciatic neuritis, mandibular joint neuralgia, peripheral neuritis, polyneuritis, stump pain, phantom limb pain, post-operative ileus, cholecystitis, postmastectomy pain syndrome, oral neuropathic pain, Charcot's pain, reflex sympathetic dystrophy, Guillain-Barre syndrome, meralgia paresthetica, burning-mouth syndrome, cluster headache, migraine headache, peripheral neuropathy, bilateral peripheral neuropathy, diabetic neuropathy, postherpetic neuralgia, trigeminal neuralgia, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, red neuralgia, Sluder's neuralgia, splenopalatine neuralgia, supraorbital neuralgia, vidian neuralgia, inflammatory bowel disease, irritable bowel syndrome, sinus headache, tension headache, labor, childbirth, menstrual cramps, and cancer.

In regard to the use of the present compounds in treatment of the diseases or conditions such as those listed above, a therapeutically effective dose can be determined by persons skilled in the art by the use of established animal models. The therapeutically effective dose of the compounds of Formula (I) exemplified in such a treatment is from about 0.001 mg/kg/day to about 300 mg/kg/day. Particularly, the range is from about 0.5 to about 5.0 mg/kg of body weight per day; and more particularly, from about 1.0 to about 3.0 mg/kg of body weight per day. The compounds may be administered on a regimen of 1 to 4 times per day.

GENERAL SYNTHETIC METHODS

Representative compounds of the present invention can be synthesized in accordance with the general synthetic methods described below and illustrated in the schemes and examples that follow. Since the schemes are an illustration, the invention should not be construed as being limited by the chemical reactions and conditions described in the schemes. The various starting materials used in the schemes and examples are commercially available or may be prepared by methods well within the skill of persons versed in the art. The variables are as defined herein.

Abbreviations used in the instant specification, particularly the schemes and examples, are as follows:

| | |
|---|---|
| AcCl | acetyl chloride |
| AcOH | glacial acetic acid |
| aq. | aqueous |
| Bn or Bzl | benzyl |
| conc. | concentrated |
| DBU | 1,8-diazabicyclo[5.4.0]undec-7-ene |
| DCM | dichloromethane |
| DMF | N,N-dimethylformamide |
| DMSO | dimethylsulfoxide |
| dppf | 1,1'-bis(diphenylphosphino)ferrocene |
| ESI | electro-spray ionization |
| EtOAc | ethyl acetate |
| EtOH | ethanol |
| h or hr | hour(s) |
| HATU | O-(1H-7-azabenzotriazol-1-yl)--1,1,3,3-tetramethyl-uronium-hexafluorophosphate |
| HPLC | high performance liquid chromatography |
| Me | methyl |
| MeOH | methanol |
| MHz | megahertz |
| min | minutes |
| MPLC | medium pressure liquid chromatography |
| MS | mass spectrometry |
| NMR | nuclear magnetic resonance |
| NT | not tested |
| Ph | phenyl |
| Pd/C | palladium on activated carbon |
| $Ph_3P$ | triphenylphosphine |
| PPA | polyphosphoric acid |
| rt | room temperature |
| TBDMS | tert-butyldimethylsilyl |
| TEA/$Et_3N$ | triethylamine |
| TFA | trifluoroacetic acid |
| THF | tetrahydrofuran |
| TLC | thin layer chromatography |
| TMS | tetramethylsilane or trimethylsilyl |

Scheme A illustrates the preparation of compounds of Formula (I)-A wherein X is O and Y is a bond; L is methylene, and $R_3$ is pyrrolidin-2-yl.

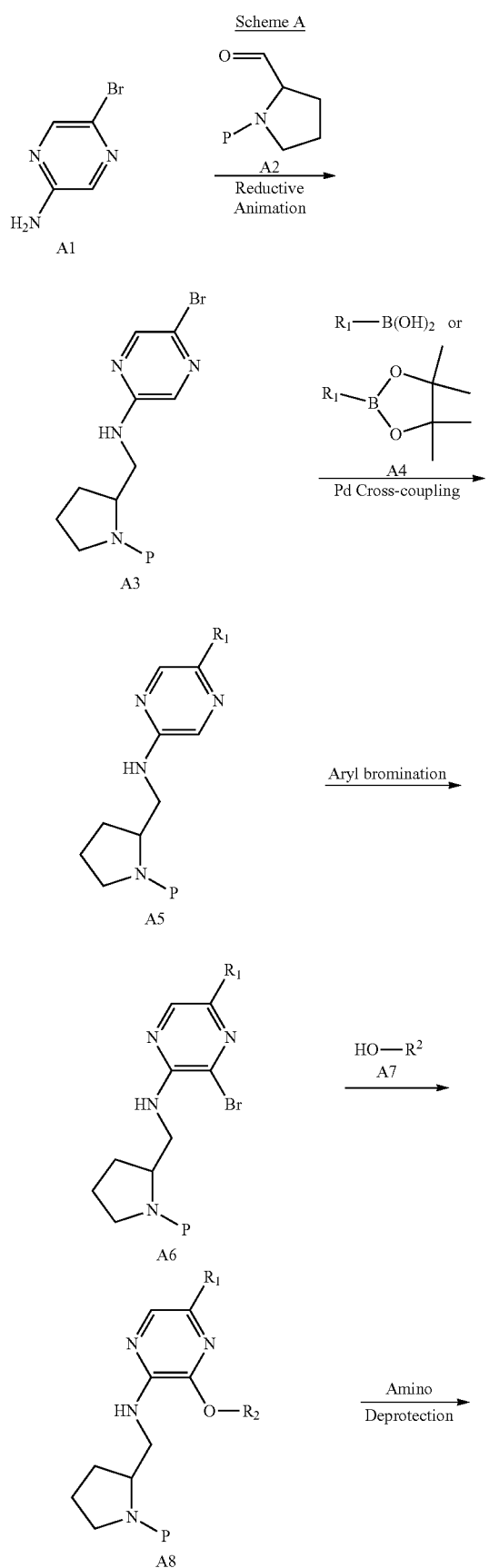

Compound A1 is either commercially available or can be made by known methods described in the scientific literature. The amino group of compound A1 may be alkylated via a reductive amination with an aldehyde of formula A2, wherein P is a conventional amino protecting group, in the presence of a hydride source, to form a compound of formula A3. The $R_1$ group of formula (I) may be introduced through a palladium catalyzed cross-coupling with an appropriately substituted boronic acid or ester (A4), in the presence of a suitable base such as potassium carbonate. The reactions also may be carried out in the presence or absence of added ligands for palladium which, when used, include one or more than one of triphenylphosphine, tri-o-tolylphosphine, tri(tert-butyl)phosphine, 1,1'-bis(diphenylphosphino)ferrocene, bis[2-(diphenyl-phosphino)phenyl]ether, 2-dicyclohexylphosphino-2',6'-dimethoxybiphenyl, 1-butyl-3-methylimidazolium hexafluorophosphate, and the like. Useful solvents include ethanol, THF, DMF, toluene, DME, dioxane, or benzene. A compound of formula A5 may be brominated in the presence of an appropriate bromination agent such as NBS to yield a compound of formula A6. Reaction with an appropriately substituted alcohol of formula A7 optionally in the presence of a base, affords a compound of formula A8. Removal of the amino-protecting group (P) using conventional methods known to those versed in the art affords a compound of formula (I)-A.

Scheme B illustrates an alternative route for the preparation of compounds of Formula (I)-A wherein X is O and Y is a bond; L is methylene, and $R_3$ is pyrrolidin-2-yl.

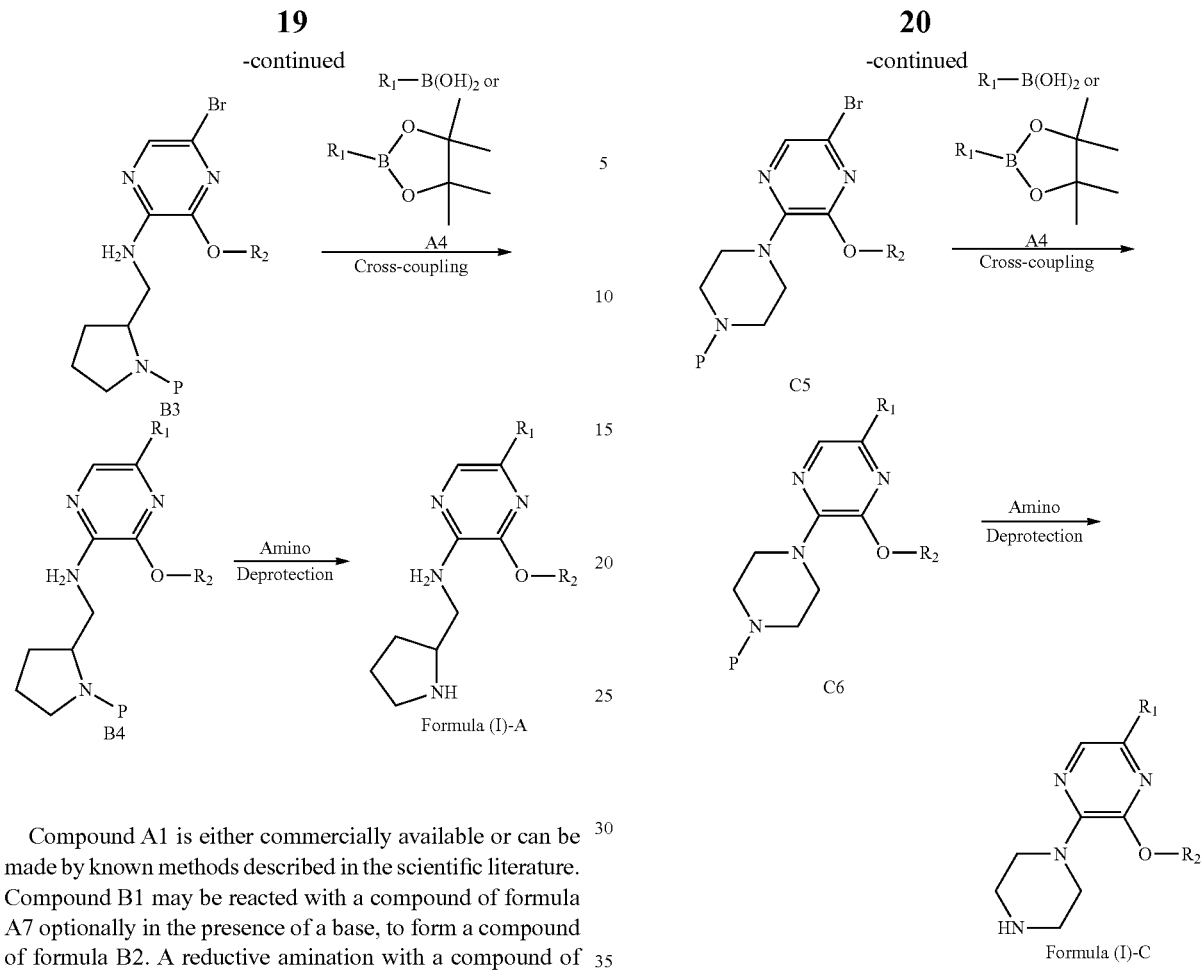

Compound A1 is either commercially available or can be made by known methods described in the scientific literature. Compound B1 may be reacted with a compound of formula A7 optionally in the presence of a base, to form a compound of formula B2. A reductive amination with a compound of formula A2 in the presence of a hydride source such sodium triacetoxyborohydride affords a compound of formula B3. A compound of formula B3 may be coupled with a boronic acid or ester of formula A4 as described in Scheme A to afford a compound of formula B4. Amino deprotection of a compound of formula B4 affords a compound of formula (I)-A.

Scheme C illustrates a route for the preparation of compounds of Formula (I)-C wherein X is O and Y is a bond; and $R_3$ is taken with L and the nitrogen atom to which L is attached to form a piperazinyl ring.

Scheme C

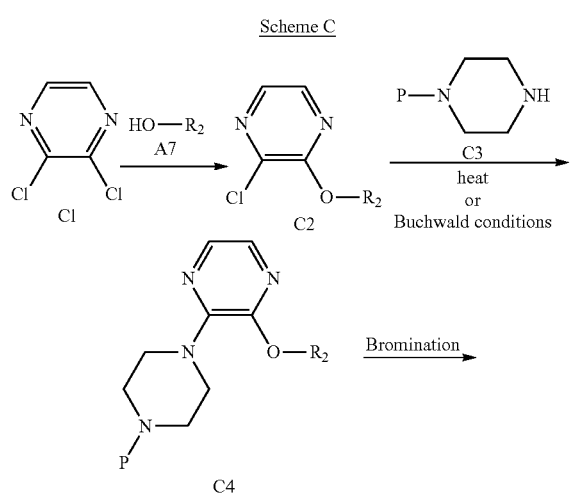

The compound C1 is either commercially available or can be made by known methods described in the scientific literature. The compound C1 may undergo an aromatic nucleophilic substitution with a compound of formula A7 optionally in the presence of a base, to form a compound of formula C2. Upon heating a compound of formula C2 with an amine of formula C3, a compound of formula C4 may be prepared. A compound of formula C4 may also be prepared by treating a compound of formula C2 with an amine of formula C3 in the presence of a palladium catalyst and appropriate ligands. Aromatic bromination with a brominating agent such as NBS affords a compound of formula C5. The bromide of formula C5 may participate in a palladium catalyzed cross coupling reaction, as described herein, to form a compound of formula C6. Amino deprotection affords a compound of formula (I)-C.

Scheme D illustrates a route for the preparation of compounds of Formula (I)-D wherein X is $CH_2$ and Y is a bond; and L is methylene, and $R_3$ is pyrrolidin-2-yl.

Scheme D

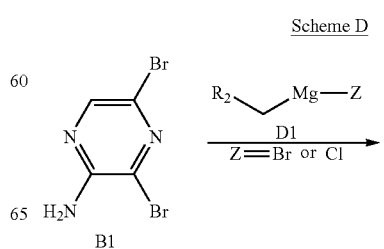

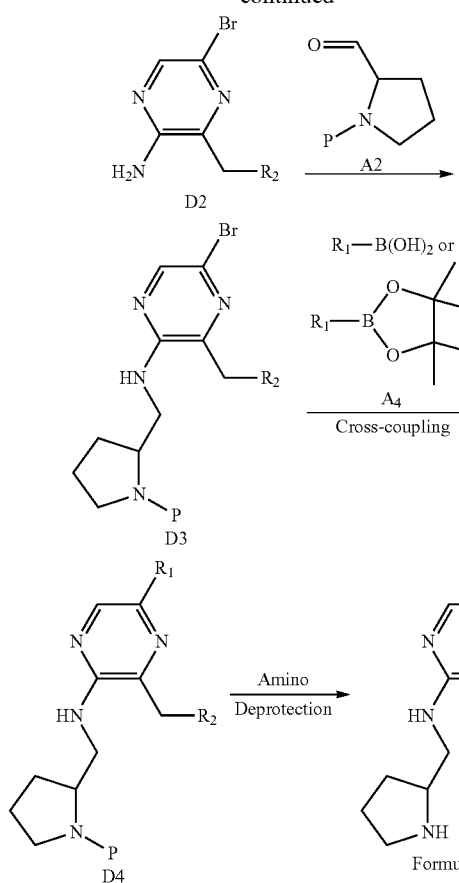

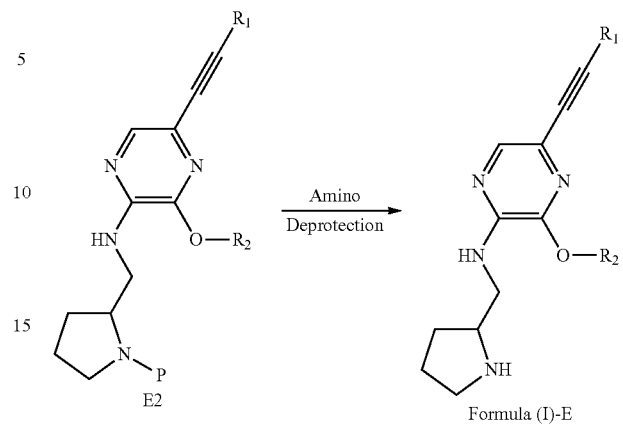

The compound of formula B3 may be coupled with a commercially available R$_1$-substituted ethyne of formula E1, in the presence of a palladium catalyst and copper iodide, and an organic base such as TEA to afford a compound of formula E2. Conventional amino deprotection affords a compound of formula (I)-E.

Scheme F illustrates a route for the preparation of compounds of Formula (I)-E wherein X is O and Y is ethynyl, L is CH$_2$, and R$_3$ is pyrrolidin-2-yl The compound B1 may be alkylated with an appropriately substituted R$_2$-methylmagnesium halide of formula D1 in an aprotic solvent such as THF, and in the presence of zinc chloride and a palladium catalyst to afford a compound of formula D2. Reductive alkylation with a compound of formula A2 affords a compound of formula D3. R$_1$ may be installed via a palladium catalyzed cross coupling reaction with a compound of formula A4 as described herein to afford a compound of formula D4. Amino deprotection affords a compound of formula (I)-D.

Scheme E illustrates a route for the preparation of compounds of Formula (I)-E wherein X is O and Y is ethynyl, L is methylene, and R$_3$ is pyrrolidin-2-yl.

Scheme E

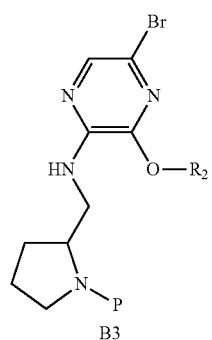

Scheme F

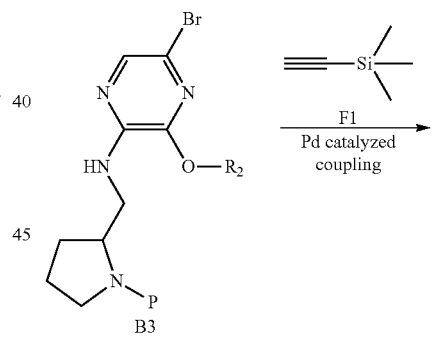

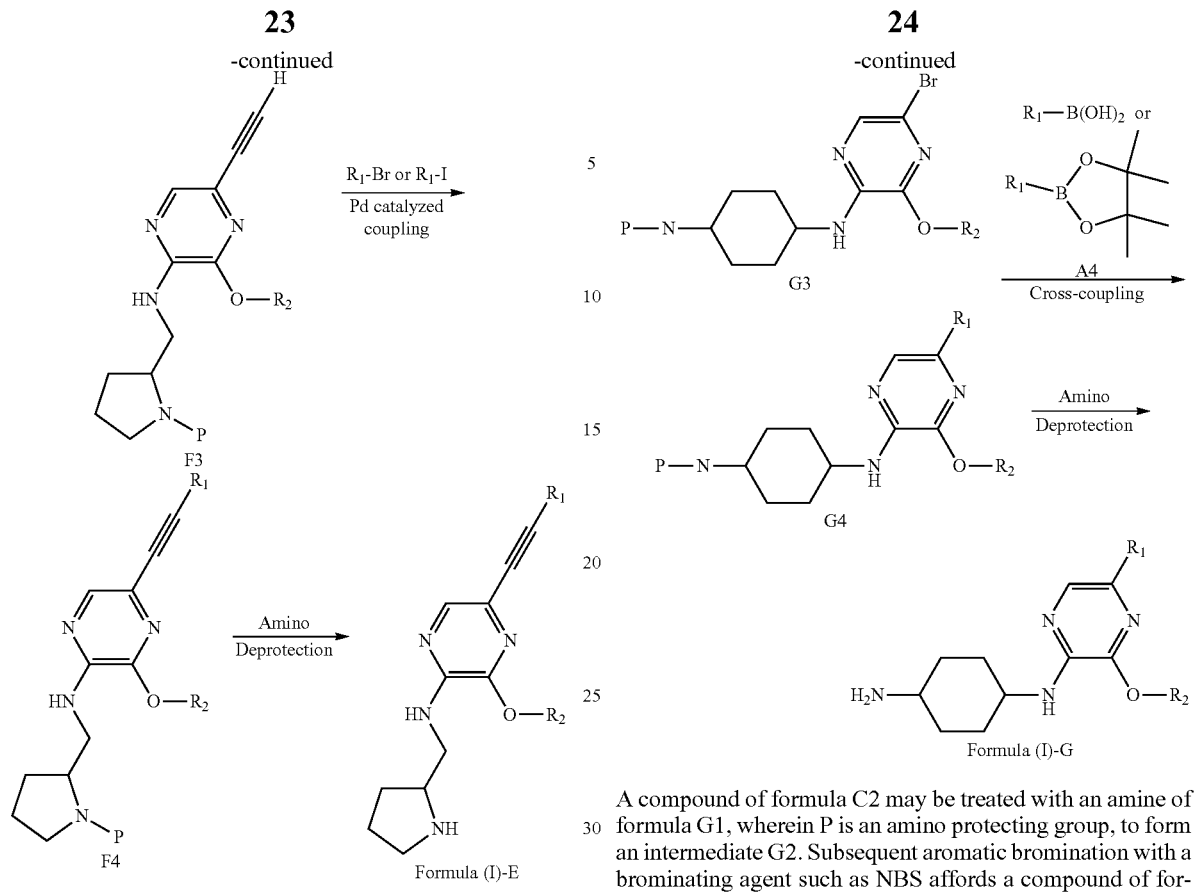

The compound of formula B3 may be coupled with a TMS-protected alkyne of formula F1, in the presence of a palladium catalyst and copper iodide, and an organic base such as TEA to afford a compound of formula F2. Removal of the TMS group using a fluoride source such as TBAF affords a compound of formula F3. A compound of formula F3 may be coupled with an $R_1$ bromide or iodide in the presence of a palladium catalyst and copper iodide, and an organic base such as TEA to afford a compound of formula F4. Conventional amino deprotection affords a compound of formula (I)-E.

Scheme G illustrates a route for the preparation of compounds of Formula (I)-G wherein X is O and Y is a bond; L is absent, and $R_3$ is 4-amino-cyclohexyl.

A compound of formula C2 may be treated with an amine of formula G1, wherein P is an amino protecting group, to form an intermediate G2. Subsequent aromatic bromination with a brominating agent such as NBS affords a compound of formula G3. The bromide of formula G3 may participate in a palladium catalyzed cross coupling reaction, as described herein, to form a compound of formula G4. Conventional removal of the amino protecting group (P) affords compounds of formula (I)-G of the present invention.

Scheme H illustrates a route for the preparation of compounds of Formula (I)-H wherein X is O and Y is a bond; L is methylene, and $R_3$ is 1-amino-eth-1-yl or 1-amino-cyclopent-1-yl.

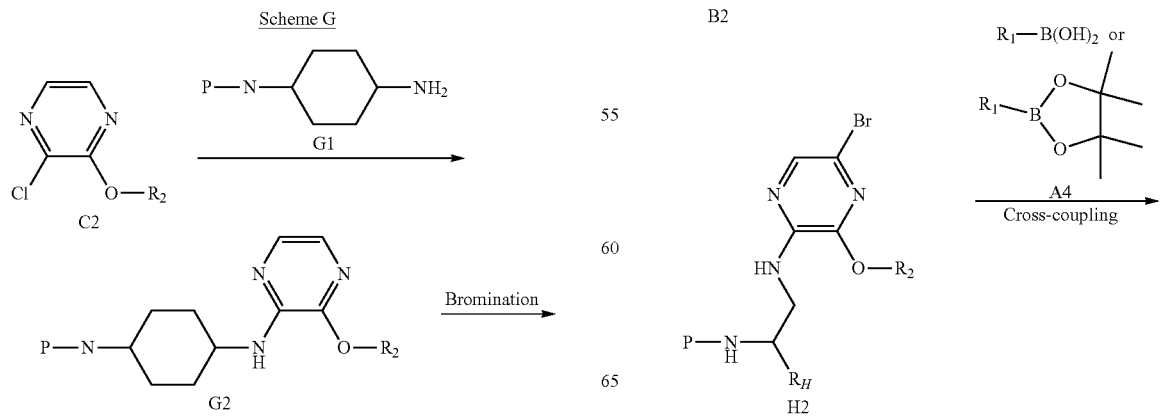

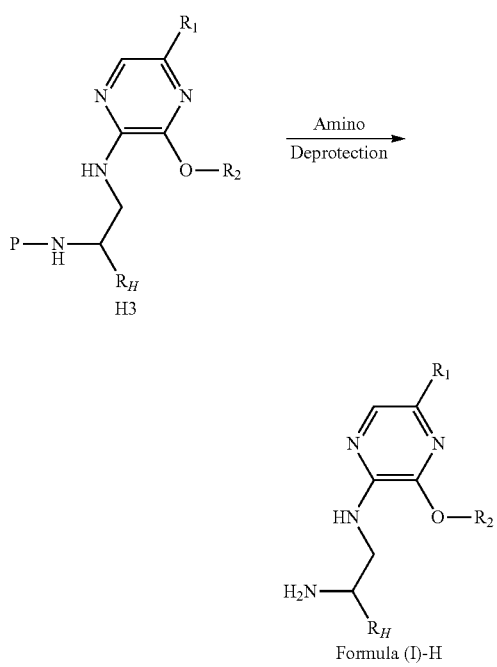

Formula (I)-H $R_H$ is methyl or spirofused cyclopentyl

A compound of formula B2 may be condensed with an aldehyde of formula H1 in the presence of a hydride source, wherein $R_H$ is methyl or spirofused cyclopentyl, to form an intermediate H2. Aldehydes of formula H1 are either commercially available or may be prepared from the reduction of its corresponding carboxylic acid. The bromide of formula H2 may participate in a palladium catalyzed cross coupling reaction, as described herein, with a boronic acid or ester of formula A4 to form a compound of formula H3. Conventional removal of the amino protecting group (P) affords compounds of formula (I)-H of the present invention.

Scheme I illustrates a route for the preparation of compounds of Formula (I)-I wherein X is $CH_2$ and Y is ethynyl, L is methylene, and $R_3$ is pyrrolidin-2-yl.

Scheme I

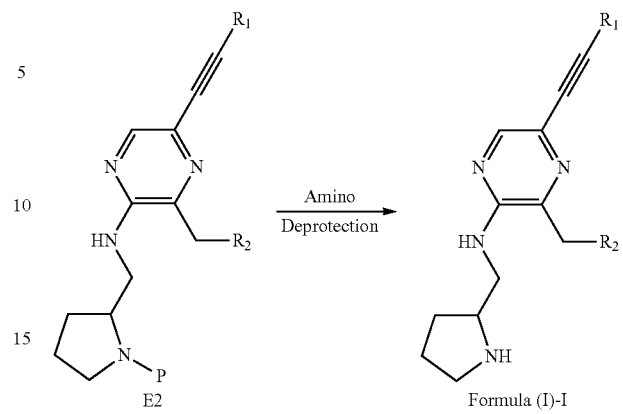

A compound of formula D3 may be coupled with a commercially available $R_1$-substituted ethyne of formula E1, in the presence of a palladium catalyst and copper iodide, and an organic base such as TEA to afford a compound of formula I1. Conventional amino deprotection affords a compound of formula (I)-I.

SPECIFIC EXAMPLES

Reagents were purchased from commercial sources. Nuclear magnetic resonance (NMR) spectra for hydrogen atoms were measured in the indicated solvent with tetramethylsilane (TMS) as the internal standard on a Bruker Avance or Varian (300 or 400 MHz) spectrometer. The values are expressed in parts per million downfield from TMS. The mass spectra (MS) were determined on a Micromass Platform LC or Agilent 1100 LCMS spectrometer as (ESI) m/z (M–H$^+$) using an electrospray technique. Microwave accelerated reactions were performed using a CEM Discover or Biotage microwave instrument, and were contained in a sealed pressure vessel unless otherwise noted. Stereoisomeric compounds may be characterized as racemic mixtures or as separate diastereomers and enantiomers thereof using X-ray crystallography and other methods known to one skilled in the art. Unless otherwise noted, the materials used in the examples were obtained from readily available commercial suppliers or synthesized by standard methods known to one skilled in the art of chemical synthesis. The substituent groups, which vary between examples, are hydrogen unless otherwise noted.

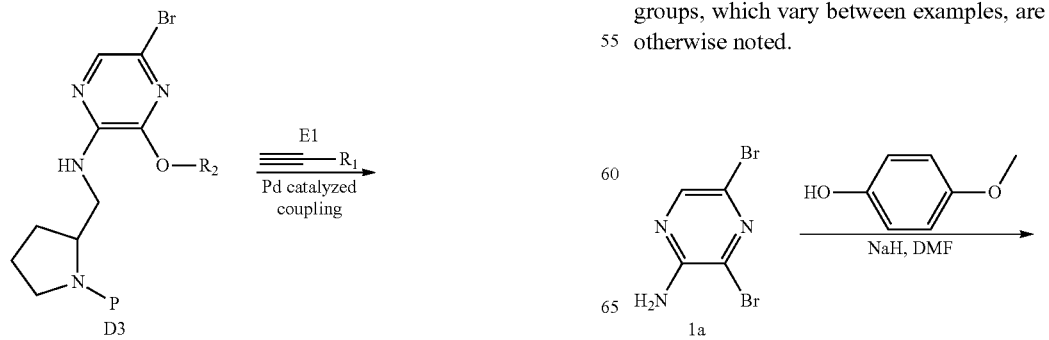

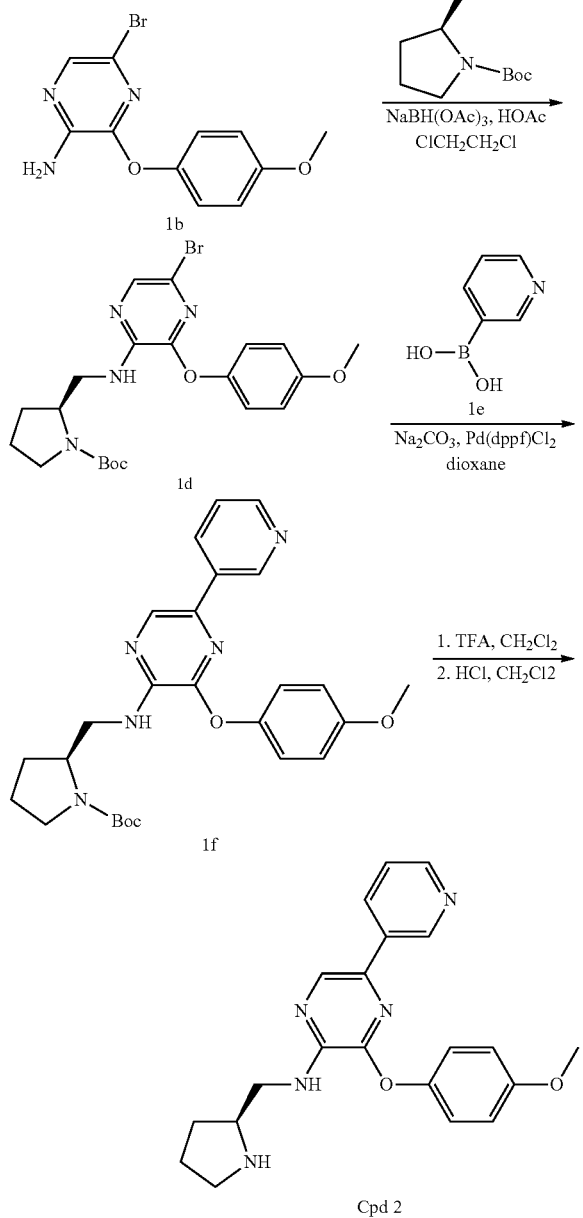

A. 5-Bromo-3-(4-methoxy-phenoxy)-pyrazin-2-ylamine (1b). To a suspension of NaH (60% in mineral oil) (0.264 g; 6.6 mmol) in DMF (13 mL) was added a solution of 4-methoxy phenol (0.63 g; 5.08 mmol) in DMF (2 mL) dropwise. The mixture was stirred at room temperature for 30 minutes under an argon atmosphere. A solution of 3,5-dibromo-pyrazin-2-ylamine (Compound 1a, 1.285 g; 5.08 mmol) in DMF (5 mL) was added to the reaction mixture, and the resulting mixture was heated at 70° C. for 1 h. The mixture was allowed to cool to room temperature, and was then quenched with ice water and stirred for 10 minutes. The solid was collected by filtration to afford a solid (dark brown). The precipitate was dissolved in EtOAc, then recrystallized from $Et_2O$-hexanes to afford Compound 1b (0.784 g; 52% yield) as an orange solid. $^1$H NMR (400 MHz, $CDCl_3$): δ 7.76 (s, 1H), 7.07-7.16 (m, 2H), 6.89-6.98 (m, 2H), 4.94 (br. s., 2H), 3.84 (s, 3H).

B. 2-(S)-{[5-Bromo-3-(4-methoxy-phenoxy)-pyrazin-2-ylamino]-methyl}-pyrrolidine-1-carboxylic acid tert-butyl ester (1d). To a solution of Compound 1b (0.487 g; 1.64 mmol) in 1,2-dichloroethane (7 mL) was added Boc-L-prolinal (Compound 1c) (0.557 g; 2.8 mmol) and glacial acetic acid (0.35 mL) at ambient temperature, and the resulting solution was stirred under nitrogen for 2 h. The mixture was then treated with $NaBH(OAc)_3$ (0.765 g; 3.61 mmol) and continually stirred at room temperature for 20 h. Additional Compound 1c (0.186 g; 0.93 mmol) was added to the reaction mixture, and the reaction was stirred for 2 h. The mixture was then treated with $NaB(OAc)_3H$ (0.255 g; 1.20 mmol) and continually stirred at room temperature for 20 h. The resultant mixture was diluted with $CH_2Cl_2$, washed with saturated $NaHCO_3$ (aq) and $H_2O$. The organic phase was washed sequentially with $H_2O$ and brine, and then dried over $Na_2SO_4$. The mixture was filtered and the filtrate was evaporated under reduced pressure to give the crude material. The crude material was purified by flash column chromatography ($SiO_2$), eluting with a EtOAc-hexanes gradient to afford Compound 1d (0.562 g; 72% yield). $^1$H NMR (400 MHz, $CDCl_3$): δ 7.72 (br. s., 1H), 7.12 (br. s., 2H), 6.92 (br. s., 2H), 4.20-4.51 (m, 1H), 3.83 (br. s., 3H), 3.40-3.56 (m, 4H), 1.76-2.14 (m, 4H), 1.45 (br. s., 9H).

C. 2-(S)-{[3-(4-Methoxy-phenoxy)-5-pyridin-3-yl-pyrazin-2-ylamino]-methyl}-pyrrolidine-1-carboxylic acid tert-butyl ester (1f). To a teflon-lined septum sealed Schlenk tube, a mixture of Compound 1d (160 mg; 0.334 mmol), pyridin-3-yl boronic acid (Compound 1e) (61.5 mg; 0.501 mmol), $Na_2CO_3/H_2O$ (70.8 mg; 0.668 mmol in 0.5 mL $H_2O$) and [1,1'-Bis(diphenylphosphino)-ferrocene]dichloro-palladium(II) (27.3 mg, 0.0334 mmol) in dioxane (2 mL) was heated at 85° C. for 3 h. The resultant mixture was diluted with EtOAc, washed with saturated $NH_4Cl$ (aq) and $H_2O$. The organic phase was washed with $H_2O$, and then dried over $Na_2SO_4$. The mixture was filtered and the filtrate was evaporated under reduced pressure to give a crude material. The crude material was purified by flash column chromatography ($SiO_2$), eluting with a heptane-EtOAc gradient to afford Compound 1f (80 mg; 50% yield). $^1$H-NMR (400 MHz, $CDCl_3$): δ 8.95 (s, 1H), 8.46 (d, 1H), 8.16 (s, 1H), 7.93 (d, 1H), 7.09-7.26 (m, 4H), 6.94 (d, 2H), 4.19-4.42 (m, 1H), 3.86 (s, 3H), 3.37-3.69 (m, 4H), 1.77-2.16 (m, 4H), 1.47 (s, 9H); MS: m/z 478.2 $(M+H)^+$.

D. [3-(4-Methoxy-phenoxy)-5-pyridin-3-yl-pyrazin-2-yl]-pyrrolidin-2-(S)-ylmethyl-amine (Cpd 2). To a solution of Compound 1f (80 mg; 0.157 mmol) in $CH_2Cl_2$ (1 mL) was added trifluoroacetic acid (0.7 mL) at ambient temperature. The reaction mixture was stirred at room temperature for 3 h. The reaction mixture was adjusted to pH~12 with 1 N NaOH (aq). The resultant mixture was partitioned between $CH_2Cl_2$ and $H_2O$. The organic phase was washed with $H_2O$, and dried over $Na_2SO_4$. The mixture was then filtered, and the filtrate was concentrated under reduced pressure. The residue was dissolved in $CH_2Cl_2$ (1 mL), and treated with 1.0 M HCl in $Et_2O$ (0.16 mL; 0.16 mmol) at ambient temperature. The reaction mixture was stirred at room temperature for 3 h. The reaction mixture was then concentrated in vacuo, then triturated with $Et_2O$. The solid was collected by vacuum filtration and dried to afford Compound 2 (61 mg; 94% yield) as the HCl salt. HCl salt—$^1$H-NMR (400 MHz, DMSO-$d_6$): δ 9.45 (br. s., 1H), 8.97 (s, 1H), 8.97 (br. s., 1H), 8.58 (d, 1H), 8.48 (s, 1H), 8.31 (d, 1H), 7.77 (t, 1H), 7.65 (dd, 1H), 7.26-7.33 (m, 2H), 7.01-7.07 (m, 2H), 3.82-3.89 (m, 1H), 3.80 (s, 3H), 3.72-3.78 (m, 2H), 3.12-3.29 (m, 2H), 2.03-2.13 (m, 1H), 1.82-2.02 (m, 2H), 1.69-1.81 (m, 1H); MS: m/z 378.2 $(M+H)^+$.

Following the procedure described above for Example 1 and substituting the appropriate reagents, starting materials and purification methods known to those skilled in the art, the following compounds of the present invention were prepared:

| Cpd | MS (M + H)+ |
|---|---|
| 1 | 408.2 |
| 19 | 377.2 |
| 20 | 353.2 |
| 21 | 417.2 |
| 22 | 393.2 |

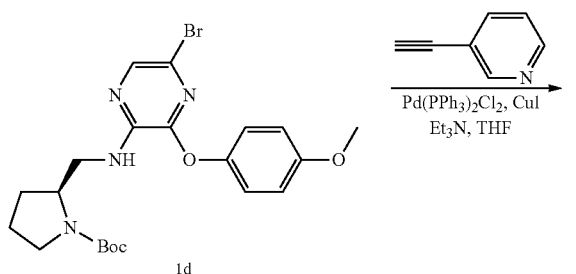

1d

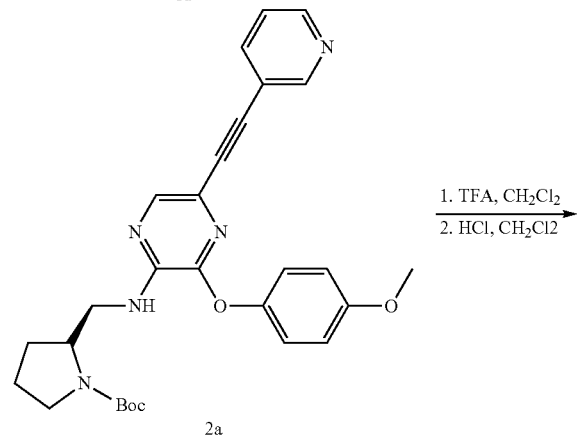

2a

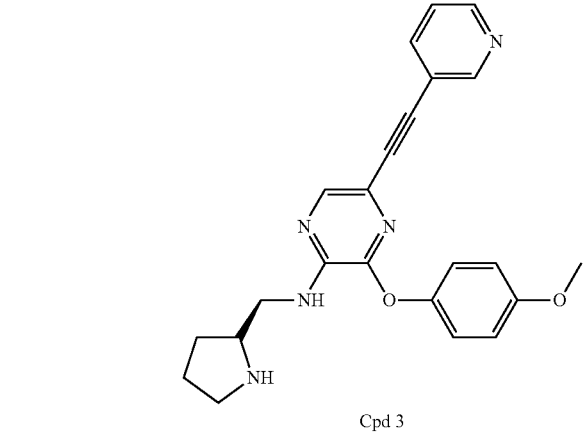

Cpd 3

A. 2-(S)-{[3-(4-Methoxy-phenoxy)-5-pyridin-3-ylethynyl-pyrazin-2-ylamino]-methyl}-pyrrolidine-1-carboxylic acid tert-butyl ester (2a). To a dry Schlenk tube was added a mixture of Compound 1d (100 mg; 0.21 mmol), 3-ethynyl-pyridine (54 mg; 0.52 mmol), copper(I) iodide (4 mg; 0.02 mmol), bis(triphenylphosphine)palladium(II) dichloride (15 mg; 0.02 mmol), and Et$_3$N (0.25 mL). The tube was sealed with a teflon-lined septum, evacuated, and refilled with argon. THF (1 mL) was added to the mixture via syringe. The mixture was heated at 70° C. for 3 h. The resultant mixture was diluted with EtOAc, washed with saturated NH$_4$Cl (aq) and H$_2$O. The organic phase was washed with H$_2$O, and then dried over Na$_2$SO$_4$. The mixture was filtered and the filtrate was concentrated under reduced pressure to give a crude material. The crude material was purified by flash column chromatography (SiO$_2$), eluting with a heptane-EtOAc gradient to afford Compound 2a (57 mg; 54% yield). $^1$H-NMR (400 MHz, CDCl$_3$): δ 8.72 (s, 1H), 8.50 (d, 1H), 7.94 (s, 1H), 7.77 (dt, 1H), 7.24 (dd, 1H), 7.07-7.20 (m, 2H), 6.92 (d, 2H), 4.18-4.39 (m, 1H), 3.83 (s, 3H), 3.35-3.67 (m, 4H), 1.75-2.15 (m, 4H), 1.45 (s, 9H).

B. [3-(4-Methoxy-phenoxy)-5-pyridin-3-ylethynyl-pyrazin-2-yl]-pyrrolidin-2-(S)-ylmethyl-amine (Cpd 3). To a solution of Compound 2a (50 mg; 0.10 mmol) in CH$_2$Cl$_2$ (1 mL) was added TFA (0.7 mL) at ambient temperature. The reaction mixture was stirred at room temperature for 3 h. The reaction mixture was adjusted to pH~12 with 1 N NaOH (aq). The resultant mixture was partitioned between CH$_2$Cl$_2$ and H$_2$O. The organic phase was washed with H$_2$O, and dried over Na$_2$SO$_4$. The mixture was then filtered, and the filtrate was concentrated under reduced pressure. The residue was dissolved in CH$_2$Cl$_2$ (1 mL), and treated with 1.0 M HCl in Et$_2$O (0.2 mL; 0.2 mmol) at ambient temperature. The reaction mixture was stirred at room temperature for 3 h. The resultant mixture was concentrated in vacuo, then triturated with Et$_2$O. The solid was collected by vacuum filtration and dried to afford Compound 3 (40 mg; 84% yield) as the HCl salt. HCl salt—$^1$H-NMR (400 MHz, DMSO-d$_6$): δ 9.39 (br. s., 1H), 8.87 (br. s., 1H), 8.78 (s, 1H), 8.62 (d, 1H), 8.07 (d, 1H), 8.03 (s, 1H), 7.92 (t, 1H), 7.53-7.58 (m, 1H), 7.17-7.22 (m, 2H), 6.99-7.05 (m, 2H), 3.80-3.85 (m, 1H), 3.78 (s, 3H), 3.71-3.76 (m, 2H), 3.11-3.28 (m, 2H), 2.02-2.12 (m, 1H), 1.83-2.01 (m, 2H), 1.67-1.79 (m, 1H); MS: m/z 402.2 (M+H)+.

Following the procedure described above for Example 2 and substituting the appropriate reagents, starting materials and purification methods known to those skilled in the art, the following compounds of the present invention were prepared:

| Cpd | MS (M + H)+ |
|---|---|
| 4 | 369.2 |

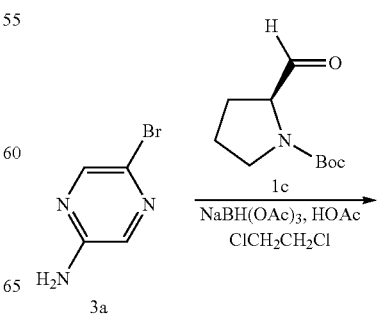

3a

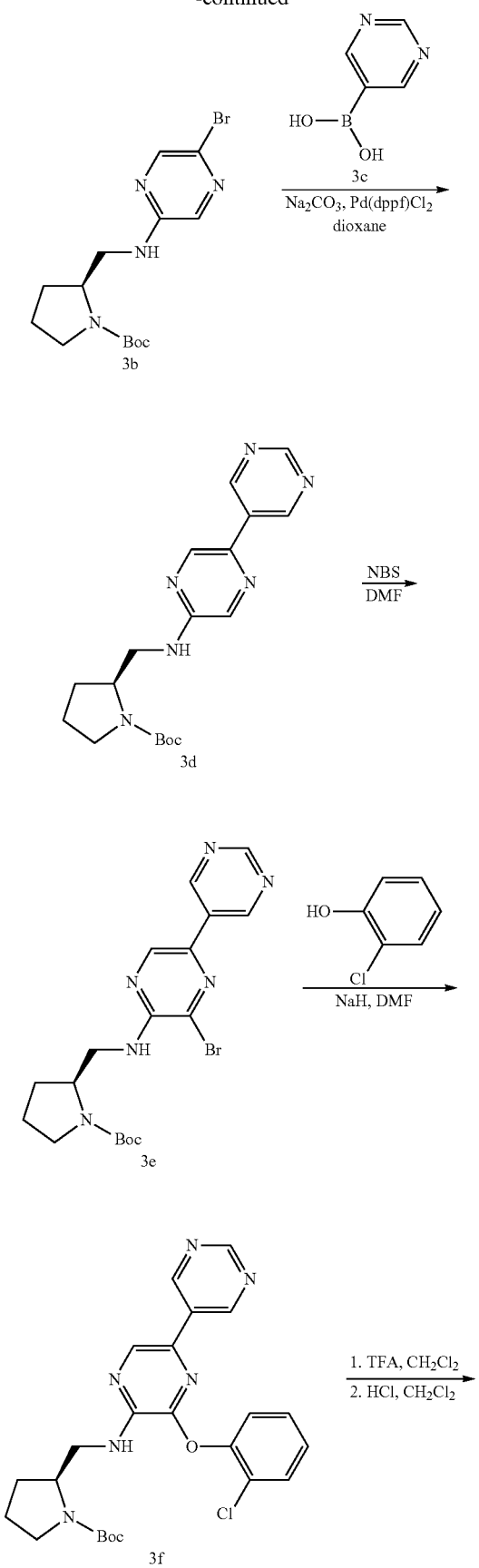
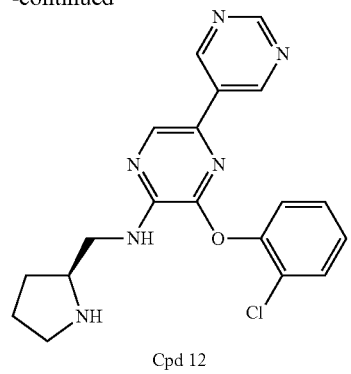

Cpd 12

A. 2-(S)-[(5-Bromo-pyrazin-2-ylamino)-methyl]-pyrrolidine-1-carboxylic acid tert-butyl ester (3b). To a solution of Compound 3a (5.75 g, 33.05 mmol) in 1,2-dichloroethane (60 mL) was added Boc-L-prolinal (Compound 1c) (9.22 g; 46.3 mmol) and glacial acetic acid (3 mL) at ambient temperature, and the resulting solution was stirred under a nitrogen atmosphere for 2 h. The mixture was then treated with NaB(OAc)$_3$H (12.6 g; 59.5 mmol) and continually stirred at room temperature for 4 h. The resultant mixture was diluted with CH$_2$Cl$_2$, washed with saturated NaHCO$_3$ (aq) and H$_2$O. The organic phase was washed sequentially with H$_2$O and brine, and then dried over Na$_2$SO$_4$. The mixture was filtered and the filtrate was concentrated under reduced pressure to give the crude material. The crude material was purified by flash column chromatography (SiO$_2$), eluting with a EtOAc-hexanes gradient to afford Compound 3b (8.97 g; 76% yield). $^1$H NMR (400 MHz, CDCl$_3$): δ 8.03 (s, 1H), 7.68 (s, 1H), 6.68 (br. s., 1H), 4.15-4.28 (m, 1H), 3.23-3.60 (m, 4H), 1.69-2.12 (m, 4H), 1.45-1.55 (m, 9H).

B. 2-(S)-[(5-Pyrimidin-5-yl-pyrazin-2-ylamino)-methyl]-pyrrolidine-1-carboxylic acid tert-butyl ester (3d). To a teflon-lined septum sealed Schlenk tube, a mixture of Compound 3b (1.742 g; 4.88 mmol), pyrimidine-5-boronic acid (Compound 3c) (0.725 g; 5.85 mmol), 1.5 M Na$_2$CO$_3$ (aq) (6.5 mL; 9.76 mmol) and [1,1'-Bis(diphenylphosphino)-ferrocene]dichliro-palladium(II) (0.32 g, 0.392 mmol) in dioxane (26 mL) was heated at 85° C. for 5 h. The resultant mixture was diluted with EtOAc, washed with saturated NH$_4$Cl (aq) and H$_2$O. The organic phase was washed with H$_2$O, and then dried over Na$_2$SO$_4$. The mixture was filtered and the filtrate was concentrated under reduced pressure to give the crude material. The crude material was purified by flash column chromatography (SiO$_2$), eluting with a heptane-EtOAc gradient to afford Compound 3d (0.8 g; 46% yield). $^1$H-NMR (400 MHz, CDCl$_3$): δ 9.20 (s, 2H), 9.17 (s, 1H), 8.43 (s, 1H), 8.02 (d, 1H), 6.99 (br. s., 1H), 4.21-4.31 (m, 1H), 3.33-3.55 (m, 4H), 2.03-2.16 (m, 1H), 1.86-2.02 (m, 2H), 1.74-1.85 (m, 1H), 1.50 (s, 9H); MS: m/z 357.2 (M+H)$^+$.

C. 2-(S)-[(3-Bromo-5-pyrimidin-5-yl-pyrazin-2-ylamino)-methyl]-pyrrolidine-1-carboxylic acid tert-butyl ester (3e). To a solution of Compound 3d (0.255 g; 0.715 mmol) in DMF (2 mL), cooled to 0° C., was added a solution of N-bromosuccinimide (140 mg; 0.786 mmol) in DMF (1 mL) dropwise under a nitrogen atmosphere. The reaction mixture was stirred at 0° C. for 2 h, then continually stirred at room temperature for 3 h. The resultant mixture was quenched with water, and extracted with Et$_2$O. The organic phase was washed sequentially with H$_2$O and brine and then dried over Na$_2$SO$_4$. The mixture was filtered and the filtrate was concentrated under reduced pressure to give the crude material. The crude material was purified by flash column chromatography (SiO$_2$), eluting with a heptane-EtOAc gradient to afford Compound 3e (0.24 g; 77% yield). $^1$H-NMR (400 MHz, CDCl$_3$): δ 9.18 (s, 2H), 9.18 (s, 1H), 8.40 (s, 1H), 7.54 (br. s., 1H), 4.30-4.39 (m, 1H), 3.34-3.60 (m, 4H), 2.04-2.16 (m, 1H), 1.88-2.02 (m, 2H), 1.72-1.84 (m, 1H), 1.51 (s, 9H); MS: m/z 435.0 (M+H)$^+$, 437.0 (M+3)$^+$.

D. 2-(S)-{[3-(2-Chloro-phenoxy)-5-pyrimidin-5-yl-pyrazin-2-ylamino]-methyl}-pyrrolidine-1-carboxylic acid tert-butyl ester (30. To a suspension of NaH (60% in mineral oil) (9.5 mg; 0.24 mmol) in DMF (1 mL) was added 2-chloro-phenol (0.03 mL; 0.26 mmol) dropwise under an argon atmosphere. The mixture was stirred at room temperature for 30 minutes. A solution of Compound 3e (80 mg; 0.184 mmol) in DMF (2 mL) was added to the reaction mixture, and the resulting mixture was heated at 90° C. for 6 h. The mixture was cooled to room temperature, then quenched with ice water and extracted with EtOAc. The organic phase was washed with H$_2$O, and then dried over Na$_2$SO$_4$. The mixture was filtered and the filtrate was concentrated under reduced pressure to give the crude material. The crude material was purified by flash column chromatography (SiO$_2$), eluting with a heptane-EtOAc gradient to afford Compound 3f (39 mg; 44% yield). MS: m/z 483.2 (M+H)$^+$.

E. [3-(2-Chloro-phenoxy)-5-pyrimidin-5-yl-pyrazin-2-yl]-pyrrolidin-2-(S)-ylmethyl-amine (Cpd 12). To a solution of Compound 3f (39 mg; 0.08 mmol) in CH$_2$Cl$_2$ (1 mL) was added trifluoroacetic acid (0.7 mL) at ambient temperature. The reaction mixture was stirred at room temperature for 3 h. The reaction mixture was adjusted to pH~12 with 1 N NaOH (aq). The resultant mixture was partitioned between CH$_2$Cl$_2$ and H$_2$O. The organic phase was washed with H$_2$O, and dried over Na$_2$SO$_4$. The mixture was then filtered, and the filtrate was concentrated under reduced pressure. The residue was dissolved in CH$_2$Cl$_2$ (1 mL), and treated with 1.0 M HCl in Et$_2$O (0.16 mL; 0.16 mmol) at ambient temperature. The reaction mixture was stirred at room temperature for 3 h. The resultant mixture was concentrated in vacuo, then triturated with Et$_2$O. The solid was collected by vacuum filtration and dried to afford Compound 12 (32 mg; 87% yield) as the HCl salt. Free base—$^1$H-NMR (400 MHz, CDCl$_3$): δ 9.06 (s, 1H), 8.95 (s, 2H), 8.21 (s, 1H), 7.48-7.54 (m, 1H), 7.32-7.38 (m, 2H), 7.23-7.29 (m, 1H), 6.09 (t, 1H), 3.72-3.82 (m, 1H), 3.58-3.67 (m, 1H), 3.43-3.54 (m, 1H), 2.98-3.13 (m, 2H), 1.98-2.09 (m, 1H), 1.75-1.97 (m, 2H), 1.54-1.67 (m, 1H); MS: m/z 383.0 (M+H)$^+$.

Following the procedure described above for Example 3 and substituting the appropriate reagents, starting materials and purification methods known to those skilled in the art, the following compounds of the present invention were prepared:

| Cpd | MS (M + H)$^+$ |
|---|---|
| 5 | 379.2 |
| 6 | 377.2 |
| 7 | 393.0 |
| 9 | 397.2 |
| 10 | 383.1 |
| 11 | 383.0 |
| 13 | 406.2 |
| 14 | 415.2 |
| 18 | 374.2 |
| 32 | 391.2 |

Cpd 8: Following the procedure described above for Example 3 and substituting 3-fluoro-4-methoxy-phenol[1] for 2-chloro-phenol in procedure D, the title compound was obtained. Free base—$^1$H NMR (400 MHz, CDCl$_3$): δ 9.08 (s, 1H), 9.00 (s, 2H), 8.20 (s, 1H), 6.98-7.06 (m, 3H), 5.97 (br. s., 1H), 3.95 (s, 3H), 3.70 (ddd, 1H), 3.46-3.55 (m, 1H), 3.32-3.40 (m, 1H), 2.96-3.02 (m, 2H), 1.94-2.04 (m, 1H), 1.70-1.92 (m, 2H), 1.47-1.58 (m, 1H); MS: m/z 397.2 (M+H)$^+$.

[1]3-Fluoro-4-methoxy-phenol was prepared by the following procedure:

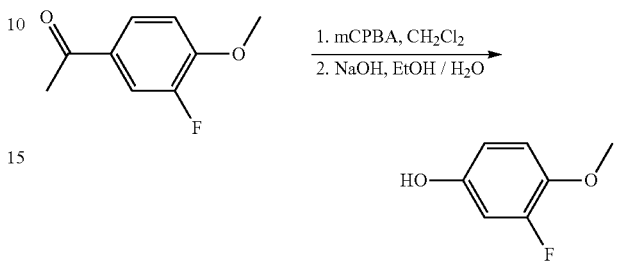

A. 3-Fluoro-4-methoxy-phenol. A mixture of 3-Fluoro-4-methoxy-acetophenone (5.16 g; 30.68 mmol) and mCPBA (8.65 g; 38.61 mmol) in CH$_2$Cl$_2$ was refluxed for 48 h. The reaction mixture was cooled to room temperature, diluted with CH$_2$Cl$_2$, washed with 5% K$_2$CO$_3$ (aq), dried over Na$_2$SO$_4$, and concentrated under reduced pressure. The residue was dissolved in ethanol (20 mL), then treated with a solution of NaOH (5.2 g) in H$_2$O (6 mL) slowly. The resultant mixture was stirred at room temperature for 3 h. The resultant mixture was concentrated and the residue was partitioned between water and Et$_2$O. The mixture was made acidic with dilute HCl (aq), and extracted with Et$_2$O. The organic phases were combined, washed with brine, dried over Na$_2$SO$_4$, and concentrated under reduced pressure to give the crude material. The crude material was stirred in hexanes, and a solid was collected by vacuum filtration to afford the title compound. $^1$H NMR (400 MHz, CDCl$_3$) δ: 6.85 (t, 1H), 6.66 (dd, 1H), 6.54 (ddd, 1H), 4.59 (br. s., 1H), 3.85 (s, 3H).

Cpd 33: Following the procedure described above for Example 3 and substituting 2,3-Dihydro-benzofuran-5-ol[2] for 2-Chloro-phenol in procedure D, the title compound was obtained. Free base—$^1$H NMR (400 MHz, CDCl$_3$): δ 9.07 (s, 1H), 9.00 (s, 2H), 8.17 (s, 1H), 7.05 (d, 1H), 6.94 (dd, 1H), 6.81 (d, 1H), 6.00 (t, 1H), 4.66 (t, 2H), 3.73 (ddd, 1H), 3.53-3.63 (m, 1H), 3.41 (ddd, 1H), 3.27 (t, 2H), 2.95-3.09 (m, 2H), 1.96-2.05 (m, 1H), 1.74-1.94 (m, 2H), 1.50-1.61 (m, 1H) MS: m/z 391.2 (M+H)$^+$.

[2]2,3-Dihydro-benzofuran-5-ol was prepared as following scheme and procedure:

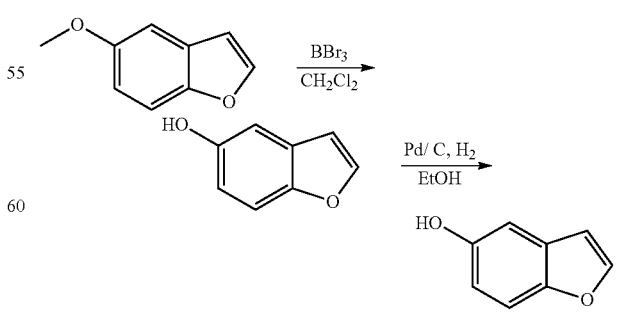

A. Benzofuran-5-ol. To a solution of BBr$_3$-SMe$_2$ (9.45 g; 30.22 mmol) in dichloroethane (50 mL) was added 5-Methoxy-benzofuran (1.28 g; 8.64 mmol), and the mixture was refluxed for 4 h under a nitrogen atmosphere. The reaction mixture was cooled to room temperature. To the resultant mixture was added water carefully, and the reaction mixture was stirred for 20 minutes. The resultant mixture was diluted with $CH_2Cl_2$, washed with brine, dried over $Na_2SO_4$, and concentrated under reduced pressure to give the crude material. The crude material was purified by flash column chromatography ($SiO_2$), eluting with a heptane-EtOAc gradient to afford the title compound. $^1$H NMR (400 MHz, $CDCl_3$) δ: 7.60 (d, J=2.3 Hz, 1H), 7.37 (d, 1H), 7.02 (d, 1H), 6.82 (dd, 1H), 6.68 (dd, 1H), 4.59 (s, 1H).

B. 2,3-Dihydro-benzofuran-5-ol. To a solution of Benzofuran-5-ol (300 mg; 2.24 mmol) in ethanol (10 mL) was added 10% Pd—C (20 mg) and the mixture was shaken under 50 psi hydrogen atmosphere in a Parr hydrogenator for 19 h. The reaction was filtered and concentrated to give a crude material. The crude material was recrystallized from toluene twice. The solid was collected by vacuum filtration and dried to give the title compound (155 mg; 51% yield). $^1$H NMR (400 MHz, $CDCl_3$): δ 6.71-6.75 (m, 1H), 6.62-6.66 (m, 1H), 6.55-6.60 (m, 1H), 4.54 (t, 2H), 4.35 (s, 1H), 3.18 (t, 2H).

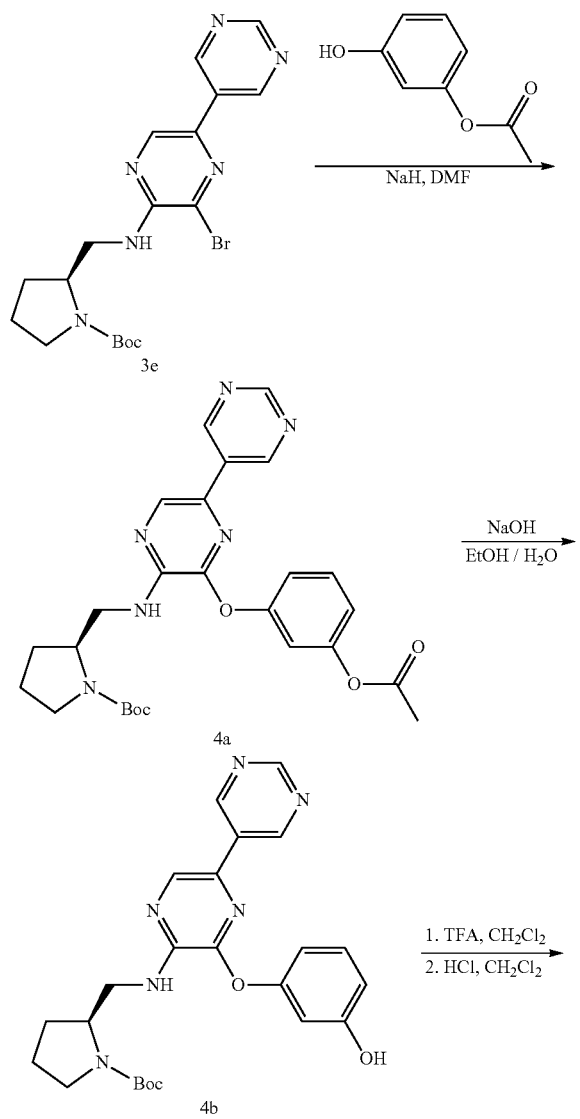

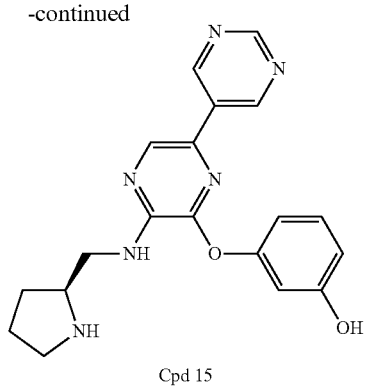

Cpd 15

A. 2-(S)-{[3-(3-Acetoxy-phenoxy)-5-pyrimidin-5-yl-pyrazin-2-ylamino]-methyl}-pyrrolidine-1-carboxylic acid tert-butyl ester (4a). To a suspension of NaH (60% in mineral oil) (18 mg; 0.45 mmol) in DMF (1 mL) was added acetic acid 3-hydroxy-phenyl ester (0.06 mL; 0.488 mmol) dropwise under an argon atmosphere. The mixture was stirred at room temperature for 30 minutes. A solution of Compound 3e (163 mg; 0.375 mmol) in DMF (2 mL) was added to the reaction mixture, and the resultant mixture was heated at 80° C. for 6 h. The mixture was allowed to cool to room temperature, then quenched with ice water and extracted with EtOAc. The organic phase was washed with $H_2O$, and then dried over $Na_2SO_4$. The mixture was filtered and the filtrate was evaporated under reduced pressure to give the crude material. The crude material was purified by flash column chromatography ($SiO_2$), eluting with a heptane-EtOAc gradient to afford Compound 4a (69 mg; 36% yield). MS: m/z 507.2 (M+H)$^+$.

B. 2-(S)-{[3-(3-Hydroxy-phenoxy)-5-pyrimidin-5-yl-pyrazin-2-ylamino]-methyl}-pyrrolidine-1-carboxylic acid tert-butyl ester (4b). To a solution of Compound 4a (20 mg) in EtOH/$H_2O$ (2/2 mL) was added 1N NaOH (aq) (2 mL), and the mixture was heated at 80° C. for 2 h. The reaction was allowed to cool to room temperature, and the organic solvent was removed. The aqueous residue was adjusted to pH ~6 with 2N HCl (aq), extracted with EtOAc, and dried over $Na_2SO_4$. The resultant mixture was concentrated and purified by preparative TLC to afford Compound 4b. $^1$H NMR (400 MHz, $CDCl_3$): δ 9.19 (s, 1H), 9.06 (s, 2H), 8.13 (s, 1H), 7.22 (t, 1H), 6.69-6.80 (m, 3H), 4.21-4.34 (m, 1H), 3.32-3.69 (m, 4H), 1.87-2.11 (m, 3H), 1.68-1.77 (m, 1H), 1.43-1.49 (m, 9H); MS: m/z 465.2 (M+H)$^+$.

C. 3-{6-Pyrimidin-5-yl-3-[(pyrrolidin-2-(S)-ylmethyl)-amino]-pyrazin-2-yloxy}-phenol (Cpd 15). To a solution of Compound 4b in $CH_2Cl_2$ (1 mL) was added trifluoroacetic acid (0.7 mL) at ambient temperature. The reaction mixture was stirred at room temperature for 3 h. The reaction mixture was adjusted to pH~12 with 1 N NaOH (aq). The resultant mixture was partitioned between $CH_2Cl_2$ and $H_2O$. The organic phase was washed with $H_2O$, and dried over $Na_2SO_4$. The mixture was then filtered, and the filtrate was concentrated under reduced pressure. The residue was dissolved in $CH_2Cl_2$ (1 mL), and treated with 1.0 M HCl in $Et_2O$ at ambient temperature. The reaction mixture was stirred at room temperature for 3 h. The resultant mixture was concentrated in vacuo, and the residue was triturated with $Et_2O$. The solid was collected by vacuum filtration and dried to afford Compound 15 as a HCl salt. Free base—$^1$H-NMR (400 MHz, $CDCl_3$): δ9.02 (s, 1H), 8.94 (s, 2H), 8.04 (s, 1H), 7.11-7.19 (m, 1H), 6.66-6.76 (m, 3H), 6.21 (t, 1H), 3.95-4.03 (m, 1H), 3.64-3.75 (m, 2H), 3.26-3.36 (m, 2H), 1.95-2.27 (m, 3H), 1.76-1.89 (m, 1H); MS: m/z 365.3 (M+H)⁺.

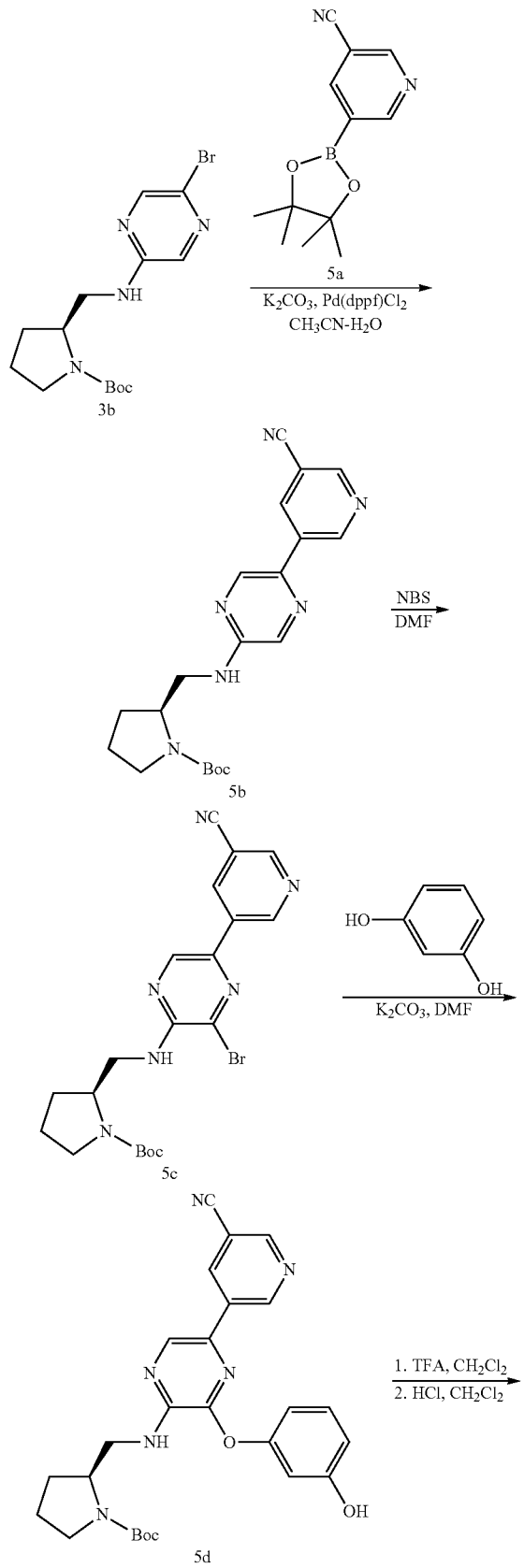

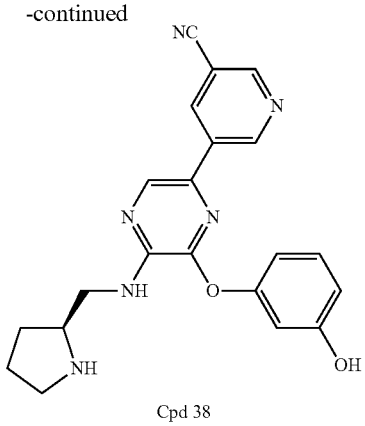

Cpd 38

A. 2-(S)-{[5-(5-Cyano-pyridin-3-yl)-pyrazin-2-ylamino]-methyl}-pyrrolidine-1-carboxylic acid tert-butyl ester (5b). To a teflon-lined septum sealed Schlenk tube, a mixture of Compound 3b (2.0 g; 5.60 mmol), 5-(4,4,5,5-tetramethyl-[1,3,2]dioxaborolan-2-yl)-nicotinonitrile (Compound 5a) (1.55 g; 6.72 mmol), K₂CO₃ (1.547 g; 11.2 mmol) and [1,1'-bis(diphenylphosphino)-ferrocene]dichloro-palladium(II) (274 mg, 0.336 mmol) in a mixture of CH₃CN (8 mL) and H₂O (2 mL) was irradiated in a microwave reactor at 140° C. for 20 minutes. The resultant mixture was diluted with EtOAc, and then washed with saturated NH₄Cl (aq) and H₂O. The organic phase was washed with H₂O, and then dried over Na₂SO₄. The mixture was filtered and the filtrate was concentrated under reduced pressure to give the crude material. The crude material was purified by flash column chromatography (SiO₂), eluting with a heptane-EtOAc gradient to afford Compound 5b (1.56 g; 73% yield) as tan powder. ¹H-NMR (400 MHz, CDCl₃): δ 9.27 (d, 1H), 8.79 (s, 1H), 8.42-8.52 (m, 2H), 8.00 (d, 1H), 7.09 (br. s., 1H), 4.05-4.34 (m, 1H), 3.30-3.59 (m, 4H), 2.03-2.17 (m, 1H), 1.86-2.01 (m, 2H), 1.73-1.84 (m, 1H), 1.50 (s, 9H); MS: m/z 381.2 (M+H)'.

B. 2-(S)-{[3-Bromo-5-(5-cyano-pyridin-3-yl)-pyrazin-2-ylamino]-methyl}-pyrrolidine-1-carboxylic acid tert-butyl ester (5c). To a solution of Compound 5b (1.53 g; 4.02 mmol) in DMF (8 mL), cooled to 0° C., was added a solution of N-bromosuccinimide (800 mg; 4.49 mmol) in DMF (6 mL) dropwise under a nitrogen atmosphere. The reaction mixture was stirred at 0° C. for 2 h, then continually stirred at room temperature for 3 h. The resulting mixture was quenched with water, and extracted with Et₂O. The organic phase was washed sequentially with H₂O, brine and then dried over Na₂SO₄. The mixture was filtered and the filtrate was concentrated under reduced pressure to give the crude material. The crude material was purified by flash column chromatography (SiO₂), eluting with a heptane-EtOAc gradient to afford Compound 5c (1.22 g; 66% yield). ¹H-NMR (400 MHz, CDCl₃): δ 9.24 (d, 1H), 8.80 (d, 1H), 8.46 (t, 1H), 8.43 (s, 1H), 7.63 (br. s., 1H), 4.10-4.41 (m, 1H), 3.32-3.62 (m, 4H), 2.04-2.20 (m, 1H), 1.85-2.03 (m, 2H), 1.71-1.85 (m, 1H), 1.44-1.54 (m, 9H); MS: m/z 459.0 (M+H)⁺, 461.0 (M+3)⁺.

C. 2-(S)-{[5-(5-Cyano-pyridin-3-yl)-3-(3-hydroxy-phenoxy)-pyrazin-2-ylamino]-methyl}-pyrrolidine-1-carboxylic acid tert-butyl ester (5d). To a teflon-lined septum sealed Schlenk tube, a mixture of Compound 5c (100 mg; 0.218 mmol), benzene-1,3-diol (150 mg; 1.362 mmol), and K₂CO₃ (60 mg; 0.434 mmol) in DMF (1 mL) was irradiated in a microwave reactor at 160° C. for 15 minutes. The resultant mixture was partitioned between Et₂O and H₂O. The organic phase was washed sequentially with H₂O, brine and then dried over Na$_2$SO$_4$. The mixture was filtered and the filtrate was concentrated under reduced pressure to give the crude material. The crude material was purified by flash column chromatography (SiO$_2$), eluting with a heptane-EtOAc gradient to afford Compound 5d (86.2 mg; 81% yield). $^1$H-NMR (400 MHz, CDCl$_3$): δ 9.12 (d, 1H), 8.70 (s, 1H), 8.12-8.26 (m, 2H), 7.42 (br. s., 1H), 7.23-7.29 (m, 1H), 6.67-6.86 (m, 3H), 5.85-6.10 (m, 1H), 4.19-4.39 (m, 1H), 3.36-3.68 (m, 4H), 1.71-2.17 (m, 4H), 1.47 (s, 9H); MS: m/z 489.2 (M+H)$^+$.

D. 5-{6-(3-Hydroxy-phenoxy)-5-[(pyrrolidin-2-(S)-ylmethyl)-amino]-pyrazin-2-yl}-nicotinonitrile (Cpd 38). To a solution of Compound 5d (86.2 mg; 0.176 mmol) in CH$_2$Cl$_2$ (3 mL) was added trifluoroacetic acid (0.4 mL) at ambient temperature. The reaction mixture was stirred at room temperature for 3 h. Removal of solvent and purification of the residue with reverse phase HPLC, eluting with a CH$_3$CN—H$_2$O gradient, afforded Compound 38 as a TFA salt (61.5 mg; 57% yield). $^1$H NMR (400 MHz, DMSO-d$_6$): δ 9.79 (s, 1H), 9.14 (d, 1H), 9.03 (br. s., 1H), 8.90 (d, 1H), 8.54 (t, 1H), 8.51 (s, 1H), 8.47 (br. s., 1H), 7.75 (t, 1H), 7.24-7.32 (m, 1H), 6.68-6.79 (m, 3H), 3.77-3.89 (m, 1H), 3.68-3.77 (m, 2H), 3.12-3.32 (m, 2H), 2.04-2.16 (m, 1H), 1.83-2.03 (m, 2H), 1.68-1.81 (m, 1H); MS: m/z 389.3 (M+H)$^+$.

Following the procedure described above for Example 5 and substituting the appropriate reagents, starting materials and purification methods known to those skilled in the art, the following compounds of the present invention were prepared:

| Cpd | MS (M + H)$^+$ |
|---|---|
| 24 | 403.2 |
| 26 | 421.2 |
| 27 | 412.2 |
| 28 | 388.2 |
| 29 | 439.0 |
| 36 | 457.0 |
| 37 | 401.2 |
| 39 | 413.0 |
| 40 | 412.2 |
| 41 | 407.0 |
| 42 | 407.0 |

Cpd 25: Following the procedure described above for Example 5 and substituting 3-fluoro-4-methoxy-phenol$^1$ for benzene-1,3-diol in procedure C, the title compound was obtained. HCl salt—$^1$H NMR (400 MHz, DMSO-d$_6$): δ 9.33 (br. s., 1H), 9.12 (br. s., 1H), 8.91 (br. s., 1H), 8.82 (br. s., 1H), 8.56 (t, 1H), 8.52 (s, 1H), 7.81 (t, 1H), 7.39 (dd, 1H), 7.24-7.31 (m, 1H), 7.15-7.21 (m, 1H), 3.88 (s, 3H), 3.79-3.86 (m, 1H), 3.71-3.78 (m, 2H), 3.11-3.30 (m, 2H), 2.02-2.14 (m, 1H), 1.82-2.01 (m, 2H), 1.68-1.81 (m, 1H); MS: m/z 421.0 (M+H)$^+$.

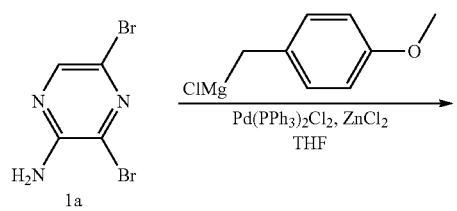

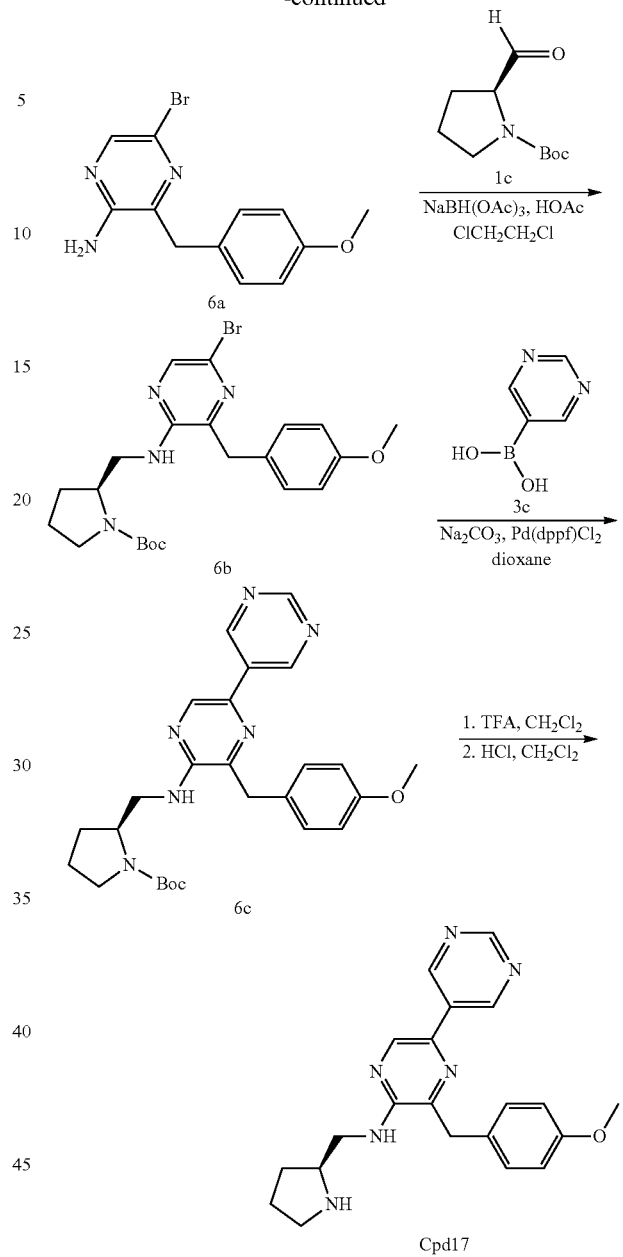

A. 5-Bromo-3-(4-methoxy-benzyl)-pyrazin-2-ylamine (6a). A solution of zinc chloride (0.5 M solution in THF) (26.3 mL; 13.23 mmol) was added to a solution of 4-methoxybenzylmagnesium chloride (0.25 M solution in THF) (50 mL; 12.5 mmol) at room temperature under a nitrogen atmosphere. The resulting turbid mixture was stirred at room temperature for 15 min. To this mixture, bis(triphenylphosphine)palladium (II) dichloride (0.185 g; 0.263 mmol) and a solution of 2-amino-3,5-dibromopyrazine (Compound 1a) (1.33 g; 5.26 mmol) in THF (4 mL) were added sequentially at room temperature. The resulting orange-colored reaction mixture was stirred for 54 h at room temperature and then quenched with water (10 mL) at 0° C. The mixture was diluted with ethyl acetate (200 mL) and water (60 mL). The organic layer was separated and the aqueous layer was extracted with ethyl acetate (2×100 mL). The combined organic layers were dried over anhydrous Na$_2$SO$_4$ and concentrated under reduced pressure. The residue was purified by flash column chromatography (SiO$_2$, 30% ethyl acetate in hexanes) to afford Compound 6a (1.36 g; 88% yield). $^1$H NMR (400 MHz, CDCl$_3$): δ8.04 (s, 1H), 7.11-7.18 (m, 2H), 6.84-6.89 (m, 2H), 4.37 (br. s., 2H), 4.03 (s, 2H), 3.80 (s, 3H).

B. 2-(S)-{[5-Bromo-3-(4-methoxy-benzyl)-pyrazin-2-ylamino]-methyl}-pyrrolidine-1-carboxylic acid tert-butyl ester (6b). To a solution of Compound 6a (1.37 g, 4.66 mmol) in 1,2-dichloroethane (30 mL) was added Boc-L-prolinal (Compound 1c) (1.114 g; 5.59 mmol) and glacial acetic acid (1.5 mL) at ambient temperature, and the reaction mixture was stirred under a nitrogen atmosphere for 2 h. The mixture was then treated with NaBH(OAc)$_3$ (1.38 g; 6.524 mmol) and continually stirred at room temperature for 20 h. Additional Compound 1c (0.56 g; 2.8 mmol) was added to the reaction mixture, and then stirred for 2 h. The mixture was then treated with NaBH(OAc)$_3$ (0.69 g; 3.26 mmol) and continually stirred at room temperature for 20 h. The resultant mixture was diluted with CH$_2$Cl$_2$, washed with saturated NaHCO$_3$ (aq) and H$_2$O. The organic phase was washed sequentially with H$_2$O and brine, and then dried over Na$_2$SO$_4$. The mixture was filtered and the filtrate was concentrated under reduced pressure to give the crude material. The crude material was purified by flash column chromatography (SiO$_2$), eluting with a EtOAc-hexanes gradient to afford Compound 6b (1.56 g; 70% yield). MS: m/z 477.1 (M+H)$^+$, 479.1 (M+3)$^+$.

C. 2-(S)-{[3-(4-Methoxy-benzyl)-5-pyrimidin-5-yl-pyrazin-2-ylamino]-methyl}-pyrrolidine-1-carboxylic acid tert-butyl ester (6c). To a teflon-lined septum sealed Schlenk tube, a mixture of Compound 6c (200 mg; 0.42 mmol), pyrimidine-5-boronic acid (Compound 3c) (78 mg; 0.63 mmol), Na$_2$CO$_3$/H$_2$O (89 mg; 0.84 mmol in 0.5 mL H$_2$O) and [1,1'-bis(diphenylphosphino)-ferrocene]dichloro-palladium(II) (34.3 mg, 0.042 mmol) in dioxane (2 mL) was heated at 100° C. for 4 h. The resultant mixture was diluted with EtOAc, washed sequentially with saturated NH$_4$Cl (aq) and H$_2$O, and then dried over Na$_2$SO$_4$. The mixture was filtered and the filtrate was concentrated under reduced pressure to give the crude material. The crude material was purified by flash column chromatography (SiO$_2$), eluting with a heptane-EtOAc gradient to afford Compound 6c (88 mg; 44% yield). $^1$H-NMR (400 MHz, CDCl$_3$): δ 9.21 (s, 2H), 9.14 (s, 1H), 8.36 (s, 1H), 7.36 (d, 2H), 7.19-7.24 (m, 1H), 6.86 (d, 2H), 4.19-4.31 (m, 1H), 4.06 (s, 2H), 3.80 (s, 3H), 3.32-3.55 (m, 4H), 2.00-2.14 (m, 1H), 1.81-2.00 (m, 2H), 1.66-1.80 (m, 1H), 1.53 (s, 9H); MS: m/z 477.3 (M+

D. [3-(4-Methoxy-benzyl)-5-pyrimidin-5-yl-pyrazin-2-yl]-pyrrolidin-2-(S)-ylmethyl-amine (Cpd 17). To a solution of Compound 6c (88 mg; 0.185 mmol) in CH$_2$Cl$_2$ (1 mL) was added trifluoroacetic acid (0.7 mL) at ambient temperature. The reaction mixture was stirred at room temperature for 3 h. The reaction mixture was adjusted to pH~12 with 1 N NaOH (aq). The resultant mixture was partitioned between CH$_2$Cl$_2$ and H$_2$O. The organic phase was washed with H$_2$O, and dried over Na$_2$SO$_4$. The mixture was then filtered, and the filtrate was concentrated under reduced pressure. The residue was dissolved in CH$_2$Cl$_2$ (1 mL), and treated with 1.0 M HCl in Et$_2$O (0.39 mL; 0.39 mmol) at ambient temperature. The reaction mixture was stirred at room temperature for 3 h. The resultant mixture was concentrated in vacuo, and the residue was triturated with Et$_2$O. The solid was collected by vacuum filtration and dried to afford Compound 17 (71 mg; 86% yield) as the HCl salt. Free base—$^1$H-NMR (400 MHz, CDCl$_3$): δ 9.21-9.25 (m, 2H), 9.17-9.20 (m, 1H), 8.35 (s, 1H), 7.21-7.26 (m, 2H), 6.81-6.86 (m, 2H), 5.97-6.14 (m, 1H), 4.16 (s, 2H), 3.90-4.01 (m, 1H), 3.68-3.81 (m, H), 3.78 (s, 3H), 3.23-3.33 (m, 1H), 2.99-3.09 (m, 1H), 2.06-2.16 (m, 1H), 1.85-1.99 (m, 2H), 1.60-1.68 (m, 2H) MS: m/z 377.3 (M+H)$^+$.

Following the procedure described for Example 6 and substituting the appropriate reagents, starting materials and purification methods known to those skilled in the art, the following compounds of the present invention were prepared:

| Cpd | MS (M + H)$^+$ |
|-----|----------------|
| 16  | 376.2          |
| 23  | 401.2          |

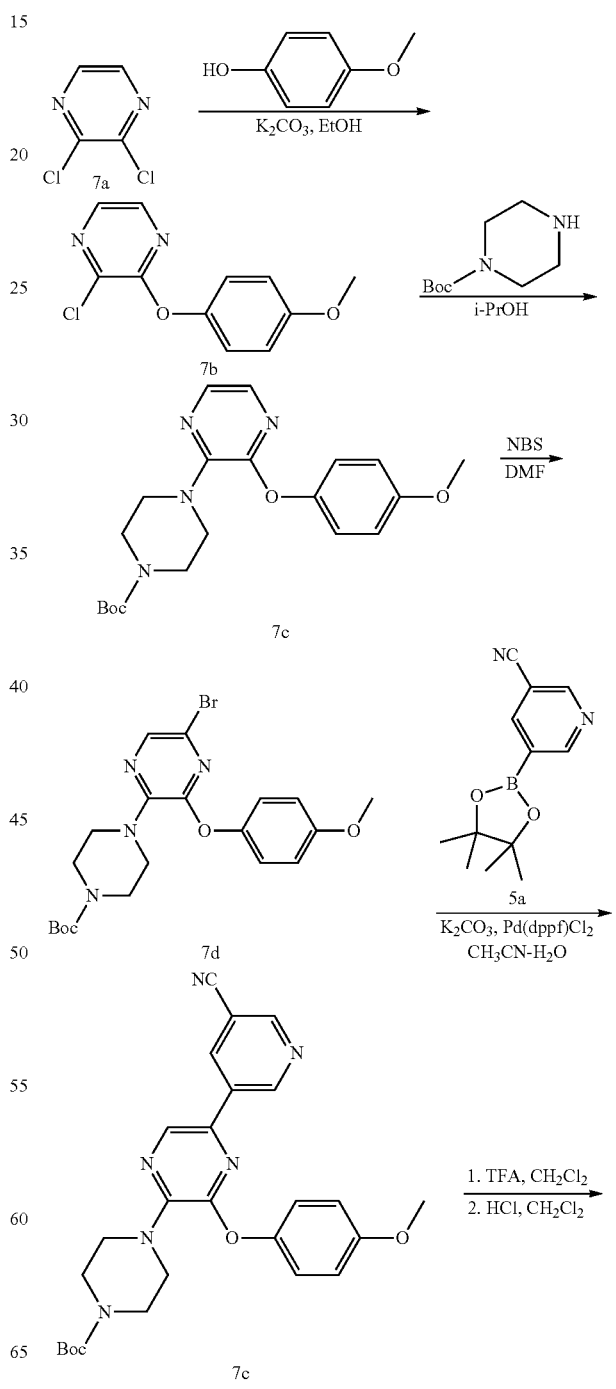

-continued

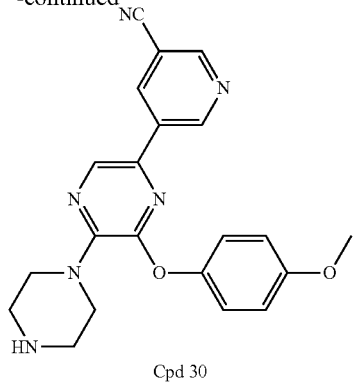
Cpd 30

A. 2-Chloro-3-(4-methoxy-phenoxy)-pyrazine (7b). A mixture of 2,3-dichloro-pyrazine (Compound 7a) (0.88 g; 5.91 mmol), 4-methoxyphenol (0.81 g; 6.5 mmol) and potassium carbonate (1.63 g; 11.82 mmol) in ethanol (20 mL) was stirred at room temperature for 20 h. The resultant mixture was concentrated in vacuo and the residue was partitioned between EtOAc and water. The organic phase was washed sequentially with diluted HCl (aq), $H_2O$, and then dried over $Na_2SO_4$. The mixture was filtered and the filtrate was concentrated under reduced pressure to give the crude material. The crude material was purified by flash column chromatography ($SiO_2$), eluting with a heptane-EtOAc gradient to afford Compound 7b (0.755 g; 54% yield). $^1$H NMR (400 MHz, $CDCl_3$): δ 8.04 (d, 1H), 7.99 (d, 1H), 7.07-7.15 (m, 2H), 6.93-7.00 (m, 2H), 3.84 (s, 3H).

B. 3'-(4-Methoxy-phenoxy)-2,3,5,6-tetrahydro-[1,2']bipyrazinyl-4-carboxylic acid tert-butyl ester (7c). In a teflon-lined septum sealed Schlenk tube, a mixture of Compound 7b (243 mg; 1.03 mmol) and piperazine-1-carboxylic acid tert-butyl ester (478 mg; 2.57 mmol) in i-PrOH/dioxane (4/0.5 mL) was heated at 98° C. for 48 h. The resultant mixture was diluted with EtOAc, washed sequentially with $H_2O$, brine and dried over $Na_2SO_4$. The mixture was filtered and the filtrate was concentrated under reduced pressure to give the crude material. The crude material was purified by flash column chromatography ($SiO_2$), eluting with a heptane-EtOAc gradient to afford Compound 7c (290 mg; 73% yield). $^1$H-NMR (400 MHz, $CDCl_3$): δ 7.82 (d, 1H), 7.54 (d, 1H), 7.05-7.09 (m, 2H), 6.93-6.98 (m, 2H), 3.83 (s, 3H), 3.60 (s, 8H), 1.50 (s, 9H).

C. 5'-Bromo-3'-(4-methoxy-phenoxy)-2,3,5,6-tetrahydro-[1,2']bipyrazinyl-4-carboxylic acid tert-butyl ester (7d). To a solution of Compound 7c (196 mg; 0.51 mmol) in DMF (2 mL), cooled to 0° C., was added a solution of N-bromosuccinimide (110 mg; 0.61 mmol) in DMF (1 mL) dropwise under a nitrogen atmosphere. The reaction mixture was stirred at 0° C. for 2 h, then continually stirred at room temperature for 3 h. The resultant mixture was quenched with water, and extracted with $Et_2O$. The organic phase was washed sequentially with $H_2O$, brine and then dried over $Na_2SO_4$. The mixture was filtered and the filtrate was concentrated under reduced pressure to give the crude material. The crude material was purified by flash column chromatography ($SiO_2$), eluting with a heptane-EtOAc gradient to afford Compound 7d (166 mg; 70% yield). $^1$H-NMR (400 MHz, $CDCl_3$): δ 7.90 (s, 1H), 7.03-7.10 (m, 2H), 6.90-6.97 (m, 2H), 3.84 (s, 3H), 3.52-3.61 (m, 8H), 1.49 (s, 9H).

D. 5'-(5-Cyano-pyridin-3-yl)-3'-(4-methoxy-phenoxy)-2,3,5,6-tetrahydro-[1,2']bipyrazinyl-4-carboxylic acid tert-butyl ester (7e). In a teflon-lined septum sealed Schlenk tube, a mixture of Compound 7d (120 mg; 0.26 mmol), Compound 5a (89 mg; 0.387 mmol), $Na_2CO_3/H_2O$ (55 mg; 0.52 mmol in 0.4 mL $H_2O$) and [1,1'-Bis(diphenylphosphino)-ferrocene] dichloro-palladium(II) (21 mg, 0.026 mmol) in dioxane (2 mL) was heated at 90° C. for 1 h. The resultant mixture was diluted with EtOAc, washed with saturated $NH_4Cl$ (aq) and $H_2O$. The organic phase was washed with $H_2O$, and then dried over $Na_2SO_4$. The mixture was filtered and the filtrate was concentrated under reduced pressure to give the crude material. The crude material was purified by flash column chromatography ($SiO_2$), eluting with a heptane-EtOAc gradient to afford Compound 7e (100 mg; 79% yield). MS: m/z 489.2 $(M+H)^+$.

E. 5-[3'-(4-Methoxy-phenoxy)-3,4,5,6-tetrahydro-2H-[1,2']bipyrazinyl-5'-yl]-nicotinonitrile (Cpd 30). Using an adaptation of the method described in Procedure D of Example 1, substituting Compound 7e for Compound 1f, the title Compound 30 was obtained as a HCl salt. Free base—$^1$H NMR (400 MHz, $CDCl_3$): δ 9.12 (d, 1H), 8.74 (d, 1H), 8.32 (s, 1H), 8.16 (t, 1H), 7.08-7.13 (m, 2H), 6.95-7.00 (m, 2H), 3.87 (s, 3H), 3.76-3.82 (m, 4H), 3.04-3.12 (m, 4H); MS: m/z 389.0 $(M+H)^+$.

Following the procedure described above for Example 7 and substituting the appropriate reagents, starting materials and purification methods known to those skilled in the art, the following compounds of the present invention were prepared:

| Cpd | MS (M + H)$^+$ |
|---|---|
| 31 | 364.2 |
| 34 | 417.2 |
| 35 | 417.2 |

Compounds 1 through 42 of Formula (I) in the table below were synthesized using the procedures described above.

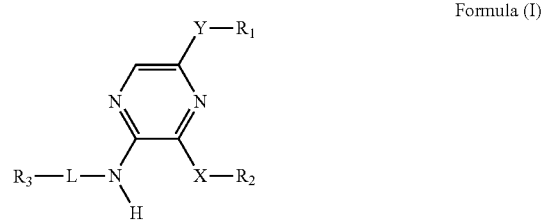

Formula (I)

TABLE 1

| Cpd | R$_1$ | Y | R$_2$ | X | L | R$_3$ | Stereo chem |
|---|---|---|---|---|---|---|---|
| 1 | 6-methoxy-pyridin-3-yl | a bond | 4-methoxyphenyl | O | methylene | pyrrolidin-2-yl | (2S) |
| 2 | pyridin-3-yl | a bond | 4-methoxyphenyl | O | methylene | pyrrolidin-2-yl | (2S) |

TABLE 1-continued

| Cpd | R₁ | Y | R₂ | X | L | R₃ | Stereo chem |
|---|---|---|---|---|---|---|---|
| 3 | pyridin-3-yl | ethynyl | 4-methoxy phenyl | O | methylene | pyrrolidin-2-yl | (2S) |
| 4 | methoxy methyl | ethynyl | 4-methoxy phenyl | O | methylene | pyrrolidin-2-yl | (2S) |
| 5 | pyrimidin-5-yl | a bond | 4-methoxy phenyl | O | methylene | pyrrolidin-2-yl | (2S) |
| 6 | pyrimidin-5-yl | a bond | 4-ethyl phenyl | O | methylene | pyrrolidin-2-yl | (2S) |
| 7 | pyrimidin-5-yl | a bond | benzo[1,3]dioxol-5-yl | O | methylene | pyrrolidin-2-yl | (2S) |
| 8 | pyrimidin-5-yl | a bond | 3-fluoro-4-methoxy phenyl | O | methylene | pyrrolidin-2-yl | (2S) |
| 9 | pyrimidin-5-yl | a bond | 2-fluoro-4-methoxy phenyl | O | methylene | pyrrolidin-2-yl | (2S) |
| 10 | pyrimidin-5-yl | a bond | 4-chloro phenyl | O | methylene | pyrrolidin-2-yl | (2S) |
| 11 | pyrimidin-5-yl | a bond | 3-chloro phenyl | O | methylene | pyrrolidin-2-yl | (2S) |
| 12 | pyrimidin-5-yl | a bond | 2-chloro phenyl | O | methylene | pyrrolidin-2-yl | (2S) |
| 13 | pyrimidin-5-yl | a bond | 3-methyl carbonyl amino-phenyl | O | methylene | pyrrolidin-2-yl | (2S) |
| 14 | pyrimidin-5-yl | a bond | 4-(1H-imidazol-1-yl) phenyl | O | methylene | pyrrolidin-2-yl | (2S) |
| 15 | pyrimidin-5-yl | a bond | 3-hydroxy phenyl | O | methylene | pyrrolidin-2-yl | (2S) |
| 16 | pyridin-3-yl | a bond | 4-methoxy phenyl | O | methylene | pyrrolidin-2-yl | (2S) |
| 17 | pyrimidin-5-yl | a bond | 4-methoxy phenyl | O | methylene | pyrrolidin-2-yl | (2S) |
| 18 | pyrimidin-5-yl | a bond | 4-cyano phenyl | O | methylene | pyrrolidin-2-yl | (2S) |
| 19 | 5-cyano-pyridin-3-yl | a bond | 4-methoxy phenyl | O | methylene | 1-amino-eth-1-yl | 1S |
| 20 | pyrimidin-5-yl | a bond | 4-methoxy phenyl | O | methylene | 1-amino-eth-1-yl | 1S |
| 21 | 5-cyano-pyridin-3-yl | a bond | 4-methoxy phenyl | O | methylene | 1-amino-cyclopent-1-yl | |
| 22 | pyrimidin-5-yl | a bond | 4-methoxy phenyl | O | methylene | 1-amino-cyclopent-1-yl | |
| 23 | 5-cyano-pyridin-3-yl | a bond | 4-methoxy phenyl | CH₂ | methylene | pyrrolidin-2-yl | (2S) |
| 24 | 5-cyano-pyridin-3-yl | a bond | 4-methoxy phenyl | O | methylene | pyrrolidin-2-yl | (2S) |
| 25 | 5-cyano-pyridin-3-yl | a bond | 3-fluoro-4-methoxy phenyl | O | methylene | pyrrolidin-2-yl | (2S) |
| 26 | 5-cyano-pyridin-3-yl | a bond | 2-fluoro-4-methoxy phenyl | O | methylene | pyrrolidin-2-yl | (2S) |
| 27 | 5-cyano-pyridin-3-yl | a bond | 4-cyano methyl-phenyl | O | methylene | pyrrolidin-2-yl | (2S) |
| 28 | 5-cyano-pyridin-3-yl | a bond | 6-methyl pyridin-3-yl | O | methylene | pyrrolidin-2-yl | (2S) |
| 29 | 5-cyano-pyridin-3-yl | a bond | 4-difluoro methoxy-phenyl | O | methylene | pyrrolidin-2-yl | (2S) |
| 30 | 5-cyano-pyridin-3-yl | a bond | 4-methoxy phenyl | O | R₃ is cyclized with L and the nitrogen atom to which L is attached to form piperazinyl | | |
| 31 | pyridin-3-yl | a bond | 4-methoxy phenyl | O | R₃ is cyclized with L and the nitrogen atom to which L is attached to form piperazinyl | | |
| 32 | pyrimidin-5-yl | a bond | benzo furan-5-yl | O | methylene | pyrrolidin-2-yl | (2S) |
| 33 | pyrimidin-5-yl | a bond | 2,3-dihydro-benzo-furan-5-yl | O | methylene | pyrrolidin-2-yl | (2S) |
| 34 | 5-cyano-pyridin-3-yl | a bond | 4-methoxy phenyl | O | absent | 4-amino-cyclohexyl | trans |

TABLE 1-continued

| Cpd | R$_1$ | Y | R$_2$ | X | L | R$_3$ | Stereo chem |
|---|---|---|---|---|---|---|---|
| 35 | 5-cyano-pyridin-3-yl | a bond | 4-methoxyphenyl | O | absent | 4-amino-cyclohexyl | cis |
| 36 | 5-cyano-pyridin-3-yl | a bond | 4-trifluoromethoxy-phenyl | O | methylene | pyrrolidin-2-yl | (2S) |
| 37 | 5-cyano-pyridin-3-yl | a bond | 4-ethylphenyl | O | methylene | pyrrolidin-2-yl | (2S) |
| 38 | 5-cyano-pyridin-3-yl | a bond | 3-hydroxyphenyl | O | methylene | pyrrolidin-2-yl | (2S) |
| 39 | 5-cyano-pyridin-3-yl | a bond | benzofuran-5-yl | O | methylene | pyrrolidin-2-yl | (2S) |
| 40 | 5-cyano-pyridin-3-yl | a bond | indol-5-yl | O | methylene | pyrrolidin-2-yl | (2S) |
| 41 | 5-cyano-pyridin-3-yl | a bond | 2-chlorophenyl | O | methylene | pyrrolidin-2-yl | (2S) |
| 42 | 5-cyano-pyridin-3-yl | a bond | 3-chlorophenyl | O | methylene | pyrrolidin-2-yl | (2S) |

BIOLOGICAL EXAMPLES

In Vitro Assays

Example 1

NG108-15, 24-Well Delta Opioid Receptor Binding Assay

Methods: NG108-15 cell membranes were purchased from Applied Cell Sciences (Rockville, Md.). 5 mg/mL of membrane protein was suspended in 10 mM TRIS-HCl pH 7.2, 2 mM EDTA, 10% sucrose. With several brief pulses from a Polytron homogenizer, each vial was homogenized in 5 mls of 50 mM Tris Buffer, pH 7.4. The homogenate was diluted in 50 mM Tris Buffer containing 5 mM MgCl$_2$ to 330 ug/ml in the working solution for a final concentration of 133 ug/well. This particulate preparation was used for the 24-well delta opioid binding assay.

Following incubation with the delta selective ligand ~0.2 nM [$^3$H]Naltrindole at 25° C. for 2.5 h in a 24-well plate with total volume of 1 mL, the plate contents were filtered through a UniFilter24, GF/B. This plate was presoaked in 0.3% PEI and filtered through a 24-well Harvester. The UniFilter24 was rinsed three times with 2 mL of 10 mM HEPES (pH 7.4), and dried in an oven at 37° C. for 1.5 hours. To each well, was added 150 μL of Scint0 (PerkinElmer, Cat#6013611). The plates were then read on a TopCount.

Analysis: The data from the scintillation counter were used to calculate either the % inhibition compared to control binding (when only a single concentration of test compound was evaluated) or a K$_i$ value (when a range of concentrations was tested). Non-specific binding (N.S. —1 mM Naloxone) was used as the negative control, while the Total Binding (T.B. —Membrane and ligand only) was used as the positive control. If one concentration was screened, the % inhibition was calculated as (cpms of total binding minus cpms of compound) divided by (cpms of T.B.minus cpms of N.S). The triplicate % Inhibitions were averaged and reported. If multiple concentrations were generated, the values were analyzed using the one-site binding non-linear regression program in Prism to determine K$_i$ values. The bottom and top values were globally shared. The triplicate K$_i$s were then averaged and reported.

The data obtained are shown in Table 2, below.

Example 2

Rat Brain Delta Opioid Receptor Binding Assay

Procedure: Male, Wistar rats (150-250 g, VAF, Charles River, Kingston, N.Y.) were killed by CO$_2$, and their brains were removed and placed immediately in ice cold Tris HCl buffer (50 mM, pH 7.4). The forebrains were separated from the remainder of the brain by a coronal transection, beginning dorsally at the colliculi and passing ventrally through the midbrain-pontine junction. After dissection, the forebrains were homogenized in Tris buffer in a Teflon®-glass homogenizer. The homogenate was diluted to a concentration of 1 g of forebrain tissue per 80 mL Tris and centrifuged at 39,000×g for 10 min. The pellet was resuspended in the same volume of Tris buffer containing 5 mM MgCl$_2$ with several brief pulses from a Polytron homogenizer. This particulate preparation was used for the delta opioid binding assays. Following incubation with the delta selective peptide ligand ~4 nM [$^3$H]DPDPE or 0.25 nM [$^3$H]naltrindole at 25° C. for 2.5 h in a 96-well plate with total volume of 1 mL, the plate contents were filtered through Wallac filtermat B sheets on a Tomtec 96-well harvester. The filters were rinsed three times with 2 mL of 10 mM HEPES (pH 7.4), and dried in a 650 W microwave oven for 1.75 min twice. To each sample area 2×50 μL of Betaplate Scint scintillation fluid (LKB) was added and the radioactivity was quantified on a LKB (Wallac) 1205 BetaPlate liquid scintillation counter.

Analysis: The data from the scintillation counter were used to calculate either the % inhibition compared to control binding (when only a single concentration of test compound was evaluated) or a K$_i$ value (when a range of concentrations was tested). Percent inhibition was calculated as: [(total dpm−test compound dpm)/(total dpm−nonspecific dpm)]*100. K$_d$ and K$_i$ values were calculated using GraphPad PRISM data analysis program. The data obtained are shown in Table 2, below.

Example 3

Rat Brain Mu Opioid Receptor Binding Assay

Procedure: Male, Wistar rats (150-250 g, VAF, Charles River, Kingston, N.Y.) were killed by CO$_2$, and their brains were removed and placed immediately in ice cold Tris HCl buffer (50 mM, pH 7.4). The forebrains were separated from the remainder of the brain by a coronal transection, beginning dorsally at the colliculi and passing ventrally through the midbrain-pontine junction. After dissection, the forebrains were homogenized in Tris buffer in a Teflon®-glass homogenizer. The homogenate was diluted to a concentration of 1 g of forebrain tissue per 80 mL Tris and centrifuged at 39,000×g for 10 min. The pellet was resuspended in the same volume of Tris buffer containing 5 mM $MgCl_2$ with several brief pulses from a Polytron homogenizer. This particulate preparation was used for the mu opioid binding assays. Following incubation with the mu selective peptide ligand, ~0.8 nM [$^3$H]DAMGO, at 25° C. for 2.5 h in a 96-well plate with total assay volume of 1 mL, the plate contents were filtered through Wallac filtermat B sheets on a Tomtec 96-well harvester. The filters were rinsed three times with 2 mL of 10 mM HEPES (pH 7.4) and dried in a 650 W microwave oven for 1.75 min twice. To each sample area 2×40 µL of Betaplate Scint scintillation fluid (LKB) was added and the radioactivity was quantifed on a LKB (Wallac) 1205 BetaPlate liquid scintillation counter.

Analysis: The data from the scintillation counter were used to calculate either the % inhibition compared to control binding (when only a single concentration of test compound was evaluated) or a $K_i$ value (when a range of concentrations was tested). Percent inhibition was calculated as: [(total dpm−test compound dpm)/(total dpm−nonspecific dpm)]*100. $K_d$ and $K_i$ values were calculated using GraphPad PRISM data analysis program. The data obtained are shown in Table 2, below.

TABLE 2

Delta and Mu Opioid Receptor Binding Data

| Cpd No. | δ-binding NG108 cell membrane $K_i$ (µM) | δ-binding (DPDPE ligand) $K_i$ (µM) | δ-binding (Naltrindole ligand) $K_i$ (µM) | µ-binding $K_i$ (µM) |
|---|---|---|---|---|
| 1 | | 0.0006 | | 2.3950 |
| 2 | | 0.0021 | | 0.8162 |
| 3 | | 0.0015 | | 3.2441 |
| 4 | | 0.0019 | | 4.9808 |
| 5 | | 0.0027 | | |
| 6 | | 0.0323 | | |
| 7 | | 0.4910 | | |
| 8 | | 0.0008 | | 0.2018 |
| 9 | | 0.0012 | | |
| 10 | | | 0.0011 | |
| 11 | | | 0.0018 | |
| 12 | | | 0.0007 | |
| 13 | | | 0.0040 | |
| 14 | | | 0.4114 | |
| 15 | | | 0.0004 | |
| 16 | | | 0.0150 | |
| 17 | | | 0.0199 | |
| 18 | | | 0.0764 | |
| 19 | | | 0.0003 | |
| 20 | | | 0.0006 | |
| 21 | | | 0.0006 | |
| 22 | | | 0.0029 | |
| 23 | | | 0.0024 | |
| 24 | | | 0.0002 | |
| 25 | | | 0.0002 | |
| 26 | | | 0.0002 | |
| 27 | | | 0.0064 | |
| 28 | | | 0.0132 | |
| 29 | | | 0.0003 | |
| 30 | | | 0.0001 | |
| 31 | | | 0.0003 | |
| 32 | | | 0.0013 | |
| 33 | | | 0.0043 | |
| 34 | | | 0.0007 | |
| 35 | | | 0.0004 | |
| 36 | | | 0.0014 | |
| 37 | | | 0.0005 | |
| 38 | | | 0.000086 | |
| 39 | | | 0.0002 | |

Example 4

[$^{35}$S]GTPγS Binding Assay in NG108-15 Cell Membranes (Delta Opioid Functional Assay)-200 nM Screen Methods: NG108-15 cell membranes were purchased from Applied Cell Sciences (Rockville, Md.). 5 mg/mL of membrane protein was suspended in 10 mM TRIS-HCl pH 7.2, 2 mM EDTA, 10% sucrose. Membranes were maintained at 4-8° C. A 1 mL volume of membranes was added into 10 mL cold binding assay buffer. The assay buffer contained 50 mM Tris, pH 7.6, 5 mM $MgCl_2$, 100 mM NaCl, 1 mM DTT and 1 mM EGTA. The membrane suspension was homogenized twice with a Polytron, and centrifuged at 3000 rpm for 10 min. The supernatant was then centrifuged at 18,000 rpm for 20 min. Ten mL of assay buffer was added into the pellet containing tube. The pellet and buffer were mixed with a Polytron.

Incubation procedure: The pellet membranes (75 µg/mL) were preincubated with SPA beads (10 mg/mL) at 25° C. for 45 min in the assay buffer. The SPA beads (5 mg/mL) coupled with membranes (37.5 µg/mL) were then incubated with 0.1 nM [$^{35}$S] GTPγS in the same Tris buffer containing 100 µM GDP in total volume of 200 µL. 200 nM of receptor agonists was used to stimulate [$^{35}$S]-GTPγS binding. The basal binding was tested in the absence of agonists and non-specific binding was tested in the presence of 10 µM unlabeled GTPγS. The data were analyzed on a Packard Top Count and are shown in Table 3, below.

Data

% of Basal=(stimulated−non specific)*100/(basal−non specific).

Relative Efficacy of a compound at 200 nM=(% of Basal of test compound at 200 nM)/(Calculated Max of SNC80 dose response. Curve in prism).

Example 5

[$^{35}$S]GTPγS Binding Assays in CHO-hMOR Cell Membranes (Mu Opioid Functional Assay)

Methods: CHO-hMOR cell membranes were purchased from Receptor Biology, Inc. (Baltimore, Md.). About 10 mg/mL of membrane protein was suspended in 10 mM TRIS-HCl pH 7.2, 2 mM EDTA, 10% sucrose, and the suspension kept on ice. A 1 mL volume of membranes was added to 15 mL cold binding assay buffer containing 50 mM HEPES, pH 7.6, 5 mM $MgCl_2$, 100 mM NaCl, 1 mM DTT and 1 mM EDTA. The membrane suspension was homogenized with a Polytron and centrifuged at 3,000 rpm for 10 min. The supernatant was then be centrifuged at 18,000 rpm for 20 min. The pellet was resuspended in 10 mL assay buffer with a Polytron. The membranes were preincubated with wheat germ agglutinin coated SPA beads (Amersham) at 25° C. for 45 min in the assay buffer. The SPA bead (5 mg/mL) coupled membranes (10 µg/mL) were then incubated with 0.5 nM [$^{35}$S] GTPγS in the assay buffer. The basal binding was that taking place in the absence of added test compound; this unmodulated binding was considered as 100%, with agonist stimulated binding rising to levels significantly above this value. A range of concentrations of receptor agonist was used to stimulate [$^{35}$S]GTPγS binding. Both basal and non-specific binding were tested in the absence of agonist; non-specific binding determination included 10 µM unlabeled GTPγS.

Compounds were tested for function as antagonists by evaluating their potential to inhibit agonist-stimulated GTPγS binding. Radioactivity was quantified on a Packard Top-Count. The following parameters were calculated:

$$\% \text{ stimulation} = \frac{(\text{test compound } cpm - \text{non-specific } cpm)}{(\text{basal } cpm - \text{non-specific } cpm)} \times 100$$

$$\% \text{ inhibition} = \frac{(\% \text{ stimulation by } 1 \ \mu M \ DAMGO - \% \text{ stimulation by test compound})}{(\% \text{ stimulation by } 1 \ \mu M \ DAMGO - 100)} \times 100$$

$EC_{50}$ values were calculated using GraphPad Prism and are shown in Table 3, below.

TABLE 3

Delta and Mu Opioid Receptor Functional Data

| Cpd No. | GTPγS δ-Rel-Efficacy @200 nM | GTPγS δ-opioid receptor $EC_{50}$ (μM) | GTPγS δ-opioid receptor Rel Efficacy | GTPγS δ-opioid receptor % Inh @10 μM | GTPγS μ-opioid receptor $EC_{50}$ (μM) | GTPγS μ-opioid receptor % Inh @10 μM |
|---|---|---|---|---|---|---|
| 1 | | 0.0585 | 0.8696 | 6.5738 | | |
| 2 | | 0.0297 | 1.0430 | 1.0000 | | |
| 3 | | 0.0462 | 1.0797 | 1.0000 | | |
| 4 | | 0.0825 | 0.9477 | 1.0000 | | |
| 5 | | 0.3486 | 1.0984 | | | |
| 6 | | 0.4597 | 1.1553 | | | |
| 8 | | 0.1478 | 1.0302 | | | |
| 9 | | 0.2811 | 1.1022 | | | |
| 10 | 0.2150 | | | | | |
| 11 | 0.2102 | | | | | |
| 12 | 0.2356 | | | | | |
| 13 | 0.0800 | | | | | |
| 16 | | 7.3198 | 0.3985 | | | |
| 17 | 0.1065 | | | | | |
| 18 | 0.1065 | | | | | |
| 20 | 0.6890 | 0.0505 | 1.0287 | | | |
| 21 | 0.2481 | | | | | |
| 22 | 0.2384 | | | | | |
| 23 | 0.1174 | | | | | |
| 24 | 0.1669 | | | | | |
| 25 | 0.9130 | 0.0313 | 1.0387 | | | |
| 26 | 1.0180 | 0.0271 | 1.0534 | | | |
| 27 | 0.9179 | 0.0342 | 1.0035 | | | |
| 28 | 0.1492 | | | | | |
| 29 | 0.0000 | | | | | |
| 30 | 0.5999 | 0.1111 | 1.1345 | | | |
| 31 | 0.7579 | 0.0081 | 1.0012 | | | |
| 32 | 0.5502 | 0.0793 | 1.0487 | | | |
| 35 | 0.4157 | 0.0952 | 1.2053 | | | |
| 36 | 0.5598 | 0.0297 | 0.9719 | | | |
| 37 | 0.3353 | | | | | |
| 38 | 0.6472 | 0.0666 | 1.1104 | | | |
| 39 | 1.0765 | 0.0046 | 1.0736 | | | |
| 40 | 0.6606 | 0.0393 | 1.1190 | | | |
| 41 | 0.3049 | 0.2981 | 1.2922 | | | |
| 42 | 0.7111 | 0.0844 | 1.1894 | | | |

In Vivo Assay

Example 6

Rat CFA Radiant Heat Model of Inflammatory Pain

Intraplantar injection of Complete Freund's Adjuvant (CFA) in rodents results in a strong, long-lasting inflammatory reaction, characterized by a chronic and pronounced hyperalgesia to both thermal and mechanical stimuli. These effects peak between 24-72 h following injection, and can last for several days to a few weeks. To assess the ability of compounds to reverse thermal hyperalgesia, male Sprague-Dawley rats (200-350 g) may be given an intraplantar injection of CFA (1:1 CFA:saline, 100 μL) into their left hindpaw. Following a 24-h incubation period, response latencies on the Radiant Heat Paw Stimulator (RH) were obtained and compared to baseline (pre-CFA) latencies. The RH device automatically registered lifting of the paw from the surface of the glass. Only rats that exhibited at least a 25% reduction in response latency from baseline (i.e. hyperalgesia) were included in further analysis. Following the post CFA latency assessment, rats were dosed orally (2.5 mL/kg) with test compound or vehicle (hydroxypropylmethylcellulose, HPMC). Percent reversal of hyperalgesia was calculated for each animal as (Treatment Response−postCFA Response)/(preCFA Response−postCFA Response)×100. Therefore, a return to normal pre-CFA thresholds was defined as 100% efficacy, whereas no change from post-CFA thresholds was 0% efficacy. Average % reversal of hyperalgesia was then calculated for each treatment group (n=6-8 rats/group).

What is claimed is:

1. A method for treating mild to severe pain in a subject in need thereof, comprising administering to the subject a therapeutically effective amount of a compound of Formula I

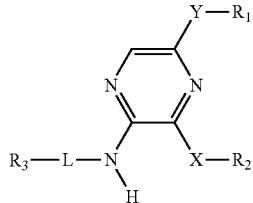

Formula I wherein
$R_1$ is selected from the group consisting of
i) phenyl optionally substituted with one to two substituents independently selected from the group consisting of $C_{1-4}$alkyl, $C_{1-4}$alkoxy, $C_{1-4}$alkylthio, hydroxy, chloro, and fluoro;
ii) pyridinyl optionally substituted with one substituent selected from the group consisting of $C_{1-4}$alkyl, $C_{1-4}$alkoxy, $C_{1-4}$alkylthio, hydroxy, fluoro, chloro, and cyano; and
iii) pyrimidin-5-yl;
or, $R_1$ is optionally methoxy-methyl when Y is ethynyl;
Y is ethynyl or a bond;
$R_2$ is phenyl, benzofuranyl, 2,3-dihydrobenzofuranyl, benzo[1,3]dioxol-5-yl, indolyl, or pyridinyl optionally substituted with methyl; wherein phenyl is optionally substituted with one to two substituents independently selected from the group consisting of $C_{1-4}$alkyl, $C_{1-4}$alkoxy, fluoro, chloro, cyano, cyanomethyl, difluoromethoxy, trifluoromethoxy, and hydroxy;
or $R_2$ is phenyl substituted with one $C_{1-4}$alkylcarbonylamino or 1H-imidazol-1-yl substituent;
X is O or $CH_2$;
L is absent and $R_3$ is 4-amino-cyclohexyl; or, L is methylene and $R_3$ is selected from the group consisting of
i) pyrrolidin-2-yl;
ii) 1-amino-eth-1-yl; and
iii) 1-amino-cyclopent-1-yl;
or, $R_3$ is cyclized with L and the nitrogen atom to which L is attached to form piperazinyl optionally substituted with 4-$C_{1-4}$alkyl;

and enantiomers, diastereomers, and pharmaceutically acceptable salts thereof.

2. The method of claim 1 wherein the mild to severe pain is due to a disease or condition selected from the group consisting of osteoarthritis, rheumatoid arthritis, fibromyalgia, migraine, headache, toothache, burn, sunburn, snake bite, spider bite, insect sting, neurogenic bladder, benign prostatic hypertrophy, interstitial cystitis, rhinitis, contact dermatitis/hypersensitivity, itch, eczema, pharyngitis, mucositis, enteritis, cellulitis, causalgia, sciatic neuritis, mandibular joint neuralgia, peripheral neuritis, polyneuritis, stump pain, phantom limb pain, post-operative ileus, cholecystitis, postmastectomy pain syndrome, oral neuropathic pain, Charcot's pain, reflex sympathetic dystrophy, Guillain-Barre syndrome, meralgia paresthetica, burning-mouth syndrome, post-herpetic neuralgia, trigeminal neuralgia, cluster headache, migraine headache, peripheral neuropathy, bilateral peripheral neuropathy, diabetic neuropathy, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, red neuralgia, Sluder's neuralgia, splenopalatine neuralgia, supraorbital neuralgia, vidian neuralgia, inflammatory bowel disease, irritable bowel syndrome, sinus headache, tension headache, labor, childbirth, menstrual cramps, and cancer.

3. The method of claim 1 wherein the pain is selected from the group consisting of inflammatory pain, centrally mediated pain, peripherally mediated pain, visceral pain, structural related pain, cancer pain, soft tissue injury related pain, progressive disease related pain, neuropathic pain and acute pain from acute injury, acute pain from trauma, acute pain from surgery, chronic pain from headache, chronic pain from neuropathic conditions, chronic pain from post-stroke conditions and chronic pain from migraine.

* * * * *